(12) United States Patent
Kramer et al.

(10) Patent No.: US 7,041,061 B2
(45) Date of Patent: May 9, 2006

(54) METHOD AND APPARATUS FOR QUANTIFICATION OF CARDIAC WALL MOTION ASYNCHRONY

(75) Inventors: Andrew P. Kramer, Stillwater, MN (US); Etienne Huvelle, Frasnes-Lez-Gosselies (BE)

(73) Assignee: Cardiac Pacemakers, Inc., Saint Paul, MN (US)

( * ) Notice: Subject to any disclaimer, the term of this patent is extended or adjusted under 35 U.S.C. 154(b) by 249 days.

(21) Appl. No.: 10/402,324

(22) Filed: Mar. 28, 2003

(65) Prior Publication Data

US 2004/0015081 A1 Jan. 22, 2004

Related U.S. Application Data

(60) Provisional application No. 60/397,189, filed on Jul. 19, 2002.

(51) Int. Cl.
*A61N 1/18* (2006.01)

(52) U.S. Cl. .................................. 600/508

(58) Field of Classification Search ............ 600/439, 600/508, 527; 607/24
See application file for complete search history.

(56) References Cited

U.S. PATENT DOCUMENTS

| | | | |
|---|---|---|---|
| 3,995,623 A | 12/1976 | Blake et al. | |
| 4,485,813 A | 12/1984 | Anderson et al. | |
| 4,674,518 A | 6/1987 | Salo | |
| 5,083,563 A | 1/1992 | Collins | |
| 5,129,394 A | 7/1992 | Mehra | |
| 5,324,326 A | 6/1994 | Lubin | |
| 5,464,434 A | 11/1995 | Alt | |
| 5,549,650 A | 8/1996 | Bornzin et al. | 607/24 |
| 5,728,140 A | 3/1998 | Salo et al. | |
| 5,755,766 A | 5/1998 | Chastain et al. | |
| 5,820,561 A * | 10/1998 | Olstad et al. | 600/453 |
| 6,044,298 A | 3/2000 | Salo et al. | |
| 6,136,021 A | 10/2000 | Tockman et al. | |
| 6,198,952 B1 | 3/2001 | Miesel | |
| 6,236,738 B1 * | 5/2001 | Zhu et al. | 382/107 |
| 6,309,350 B1 | 10/2001 | VanTassel et al. | |
| 6,398,738 B1 | 6/2002 | Millar | |
| 6,507,752 B1 * | 1/2003 | Maeda | 600/436 |

(Continued)

OTHER PUBLICATIONS

Kuecherer, H. F., et al., "Echocardiographic Fourier Phase and Amplitude Imaging for Quantification of Ischemic Regional Wall Asynergy: An Experimental Study Using Coronary Microembolization in Dogs", J of the Am College of Cardiolo, 1995, 25(6), 1436-44.*

(Continued)

*Primary Examiner*—Jeffrey R. Jastrzab
*Assistant Examiner*—Alyssa M. Alter
(74) *Attorney, Agent, or Firm*—Schwegman, Lundberg, Woessner & Kluth, P.A.

(57) ABSTRACT

A phase analysis technique provides for quantification of regional wall motion asynchrony from endocardial border contours generated from two-dimensional echocardiographic ventricular images. The technique produces results including a degree of radial ventricular asynchrony in heart failure patients with ventricular conduction delay to predict a magnitude of contractile function improvement with pacing therapy. Quantification of change in ventricular regional wall motion asynchrony in response to a therapy provides for a means to identify candidates to receive the therapy and quantitatively predict the benefit of the therapy. Quantification of changes in ventricular regional wall motion asynchrony in response to a sequence of therapies provides for a means to determine an approximately optimal therapy for an intended patient response.

20 Claims, 13 Drawing Sheets

U.S. PATENT DOCUMENTS

| | | | |
|---|---|---|---|
| 6,654,637 | B1 | 11/2003 | Rouw et al. |
| 6,832,113 | B1 | 12/2004 | Belalcazar |
| 6,892,095 | B1 | 5/2005 | Salo |
| 2002/0123769 | A1 | 9/2002 | Panken et al. |
| 2003/0130581 | A1 | 7/2003 | Salo et al. |
| 2004/0147966 | A1 | 7/2004 | Ding et al. |
| 2004/0193223 | A1 | 9/2004 | Kramer et al. |
| 2005/0102002 | A1 | 5/2005 | Salo et al. |

OTHER PUBLICATIONS

Kerwin, W. F., et al., "Ventricular Contraction Abnormalities in Dilated Cardiomyopathy: Effect of Biventricular Pacing to Correct Interventricular Dyssynchrony", Journal of the American College of Cardiology, 2000, 35 (5), 1221-1227.*

Auricchio, A., "Effect of Pacing Chamber and Atrioventricular Delay on Acute Systolic Function of Paced Patients With Congestive Heart Failure", *Circulation*, 99, (1999), 2993-3001.

Auricchio, A., "The Pacing Therapies for Congestive Heart Failure (PATH-CHF) Study: Rationale, Design, and Endpoints of a Prospective Radomized Multicenter Study", *The American Journal of Cardiology*, vol. 83, No. 5B, (Mar. 11, 1999), 130D-135D.

Bosch, J. G., et al., "Evaluation of a Semiautomatic Contour Detection Approach in Sequences of Short-Axis Two-dimensional Echocardiographic Images", *Journal of the American Society of Echocardiography*, vol. 8, No. 6, (Nov./Dec. 1995), 810-821.

Breithardt, Ole A., et al., "Acute effects of cardiac resynchronization therapy on left ventricular Doppler indices in patients with congestive heart failure", *American Heart Journal*, vol. 143, No. 1, (Jan. 2002), 34-44.

Breithardt, Ole A., et al., "Echocardiographic Quantification of Left Ventricular Asynchrony Predicts an Acute Hemodynamic Benefit of Cardiac Resynchronization Therapy", *Journal of the American College of Cardiology*, vol. 40, No. 3, (2002), 536-545.

Breithardt, Ole A., et al., "Multisite Pacing in Patients with Heart Failure Reduces Left Ventricular Asynchrony as Assessed by Echocardiographic Semiautomatic Contour Detection", *PACE*, vol. 23, (Apr. 2000), 611.

Butter, Christian, et al., "Effect of Resynchronization Therapy Stimulation Site on the Systolic Function of Heart Failure Patients", *Circulation*, 104, (2001), 3026-3029.

Fried, Ari G., et al., "Electrical and Hemodynamic Correlates of the Maximal Rate of Pressure Increase in the Human Left Ventricle", *Journal of Cardiac Failure*, vol. 5, No. 1, (Mar. 1999), 8-16.

Gomez, A. M., et al., "Defective Excitation-Contraction Coupling in Experimental Cardiac Hypertrophy and Heart Failure", *Science*, vol. 276, (May 2, 1997), 800-806.

Grines, Cindy L., et al., "Functional Abnormalities in Isolated Left Bundle Branch Block. The Effect of Interventricular Asynchrony.", *Circulation*, vol. 79, No. 4, (Apr. 1989), 845-853.

Hansen, Alexander, et al., "Echocardiographic quantification of left ventricular asynergy in coronary artery disease with Fourier phase imaging", *The International Journal of Cardiovascular Imaging*, vol. 17, No. 2, (Apr. 2001), 81-88.

Kass, David A., et al., "Improved Left Ventricular Mechanics From Acute VDD Pacing in Patients with Dilated Cardiomyopathy and Ventricular Conduction Delay", *Circulation*, 99, (Mar. 30, 1999), 1567-1573.

Kawaguchi, Miho, et al., "Quantitation of Basal Dyssynchrony and Acute Resychronization from Left or Biventricular Pacing by Novel Echo-Contrast Variability Imaging", *Journal of the American College of Cardiology*, vol. 39, No. 12, (2002), 2052-2058.

Kerwin, Walter F., et al., "Ventricular Contraction Abnormalities in Dilated Cardiomyopathy: Effect of Biventricular Pacing to Correct Interventricular Dyssynchrony", *Journal of the American College of Cardiology*, vol. 35, No. 5, (2000), 1221-1227.

Le Rest, Catherine, et al., "Use of left ventricular pacing in heart failure: Evaluation by gated blood pool imaging", *Journal of Nuclear Cardiology*, vol. 6, No. 6, (Nov./Dec. 1999),651-656.

Li, Yun You, et al., "Downregulation of Matrix Metalloproteinases and Reduction in Collagen Damage in the Failing Human Heart After Support With Left Ventricular Assist Devices", *Circulation*, 104, (Sep. 4, 2001), 1147-1152.

Nelson, Gregory S., et al., "Left Ventricular or Biventricular Pacing Improves Cardiac Function at Diminished Energy Cost in Patients with Dilated Cardiomyopathy and Left Bundle-Branch Block", *Circulation*, 102, (2000), 3053-3059.

Nelson, Gregory S., et al., "Predictors of Systolic Augmentation From Left Ventricular Preexcitation in Patients with Dilated Cardiomyopathy and Intraventricular Conduction Delay", *Circulation*, 101, (Jun. 13, 2000), 2703-2709.

Prinzen, Frits W., et al., "Mapping of Regional Myocardial Strain and Work During Ventricular Pacing: Experimental Study Using Magnetic Resonance Imaging Tagging", *Journal of the American College of Cardiology*, vol. 33, No. 6, (May 1999), 1735-1742.

Sogaard, Peter, et al., "Impact of Acute Biventricular Pacing on Left Ventricular Performance and Volumes in Patients with Severe Heart Failure: a tissue Doppler and three-dimensional echocardiographic study", *Cardiology*, 95, (2001), 173-182.

Stellbrink, Christoph, et al., "Impact of Cardiac Resynchronization Therapy Using Hemodynamically Optimized Pacing on Left Ventricular Remodeling in Patients With Congestive Heart Failure and Ventricular Conduction Disturbances", *Journal of the American College of Cardiology*, vol. 38, No. 7, (Dec. 2001), 1957-1965.

Van Oosterout, Matthijs F.M., et al., "Asynchronous Electrical Activation Induces Asymmetrical Hypertrophy of the Left Ventricular Wall", *Circulation*, 98, (Aug. 11, 1998), 588-595.

Xiao, Han B., et al., "Differing effects of right ventricular pacing and left bundle branch on left ventricular function", *British Heart Journal*, vol. 69, No. 2, (Feb. 1993), 166-173.

Yu, Cheuk-Man, et al., "Tissue Doppler Echocardiographic Evidence of Reverse Remodeling and Improved Synchronicity by Simultaneously Delaying Regional Contraction After Biventricular Pacing Therapy in Heart Failure", *Circulation*, 105, (Jan. 29, 2002), 438-445.

Kuecherer, H. F., et al., "Echocardiographic Fourier Phase and Amplitude Imaging for Quantification of Ischemic Regional Wall Asynergy: An Experimental Study Using Coronary Microembolization in Dogs", *Journal of the American College of Cardiology*, 25, No. 6, (1995), 1436-1444.

Chen, H. H., et al., "Diastolic Heart Failure in the Community: Clinical Profile, Natural History, Therapy, and Impact of Proposed Diagnostic Criteria", *Journal of Cardiac Failure*, 8(5), (2002),279-287.

Curtis, J. P., et al., "The Association of Left Ventricular Ejection Fraction, Mortality, and Cause of Death in Stable Outpatients With Heart Failure", *Journal of the American College of Cardiology*, 42(4), (2003),736-742.

Kass, D. A., "Improved Left Ventricular Mechanics From Acute VDD Pacing in Patients With Dilated Cardiomyopathy and Ventricular Conduction Delay", *Circulation*, 99(12), (Mar. 30, 1999),1567-1573.

Kim, H., et al., "Integrated MEMS for Pressure Transponder", *1997 International Conference on Solid State Sensors and Actuators. Transducers '97*, vol. 2., (Chicago, IL),(1997),1011-1014.

Little, W. C., "Clinical Evaluation of Left Ventricular Diastolic Performance", *Progress in Cardiovascular Disease*, 32(4), (1990),273-290.

Redfield, M. M., et al., "Burden of Systolic and Diastolic Ventricular Dysfunction in the Community", *JAMA*, 289(2), (2003),194-202.

Yu, C.-M., et al., "High Prevalence of Left Ventricular Systolic and Diastolic Asynchrony in Patients With Congestive Heart Failure and Normal QRS Duration", *Heart*, 89, (2003),54-60.

Zile, M.D., M. R., et al., "Diastolic Heart Failure: Diagnosis and Treatment", *Clinical Cornerstone*, 3(2), http://cardiology.medscape.com/ExcerptaMed/ClinCornerstne/200.../pnt-clc0302.03.zile.htm,((Observed Jul. 16, 2001)),14 pgs.

\* cited by examiner

METHOD AND APPARATUS FOR QUANTIFICATION OF CARDIAC WALL MOTION ASYNCHRONY

CROSS-REFERENCE TO RELATED APPLICATION(S)

This application claims the benefit of U.S. Provisional Application No. 60/397,189, filed on Jul. 19, 2002, under 35 U.S.C. § 119(e).

TECHNICAL FIELD

This document relates generally to cardiac rhythm management and particularly, but not by way of limitation, to method and system for echocardiographic quantification of cardiac wall motion.

BACKGROUND

A heart is the center of a person's circulatory system. It includes a complex electromechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. These mechanical pumping functions are accomplished by contractions of the heart. In a normal heart, the sinus node, the heart's natural pacemaker, generates electrical signals, called action potentials, that propagate through an electrical conduction system to various regions of the heart to excite the muscular tissues of these regions. Coordinated delays in the propagations of the action potentials in a normal electrical conduction system cause the various portions of the heart to contract in synchrony to result in efficient pumping functions. A blocked or otherwise abnormal electrical conduction and/or a deteriorated myocardium cause asynchronized contraction of the heart, and results in poor hemodynamic performance including diminished blood supply to the body.

Heart failure is a clinical syndrome or condition where the heart fails to supply sufficient blood to meet the metabolic needs of the body organs. It is characterized by (1) signs and symptoms of intravascular and interstitial overload, including shortness of breath, rales, and edema, or (2) manifestations of inadequate tissue perfusion, such as fatigue or poor exercise tolerance. Congestive heart failure (CHF) occurs when heart failure patients further manifest pulmonary or systemic congestion. Measurement of left ventricular performance is a critical step in evaluating and managing cardiac conditions for most heart failure patients. A specific example of heart failure is associated with left bundle branch block (LBBB), where portions of the electrical conduction system activating LV are dysfunctional. LBBB is associated with asynchronous ventricular contraction patterns and depressed ejection fraction, and is inversely correlated to the hemodynamic performance, particularly global contractile function.

Cardiac resynchronization therapy (CRT) with LV or biventricular (BV) pacing has been introduced as a complementary treatment for patients with congestive heart failure and ventricular conduction delay. CRT has been shown to improve LV systolic function as measured by peak positive LV pressure change ($dP/dt_{max}$) and Doppler echocardiography. It improves clinical symptoms of heart failure. CRT is believed to improve global ventricular function by restoring more synchronized contraction patterns, which include intraventricular synchrony. Thus, the efficacy of CRT and/or particular CRT parameters is indicated by improved ventricular synchrony.

For these and other reasons, there is a need for quantifying intraventricular asynchrony.

SUMMARY

A phase analysis technique provides for quantification of regional wall motion asynchrony from endocardial border contours generated from two-dimensional echocardiographic ventricular images. The technique produces results including a degree of radial ventricular asynchrony in heart failure patients with ventricular conduction delay to predict a magnitude of contractile function improvement with pacing therapy. Quantification of change in ventricular regional wall motion asynchrony in response to a therapy provides for a means to identify candidates to receive the therapy and quantitatively predict the benefit of the therapy. Quantification of changes in ventricular regional wall motion asynchrony in response to a sequence of therapies provides for a means to determine an approximately optimal therapy for an intended patient response.

In one embodiment, a wall motion analysis system includes a curve generator, a curve offset module, a curve averager, a curve smoothing module, and a phase computer. The curve generator generates two regional displacement curves each based on magnitudes of cardiac regional wall displacement over a cardiac cycle length interval for a cardiac region. The curve offset module provides a common magnitude reference for the two regional wall displacement curves. The curve averager averages each regional displacement curve over a predetermined number of cardiac cycles. The curve smoothing module smoothes the two averaged regional displacement curves. The phase computer computes a relative phase representing a phase relationship between the two regional displacement curves based on a frequency analysis. The relative phase quantitatively indicates cardiac wall motion asynchrony. In one embodiment, the wall motion analysis system is implemented as software residing on a computer-readable medium.

In one embodiment, a therapy evaluation system includes a controller, a therapy circuit, and the wall motion analysis system. The controller controls delivery of a sequence of therapies from the therapy circuit. The wall motion analysis system determines degrees of cardiac wall motion asynchrony in response to each therapy based on an echocardiogram recorded during the delivery of the sequence of therapies.

In one embodiment, an echocardiogram is recorded. Cardiac wall motion contours are detected from the echocardiogram. Regional displacement magnitudes are calculated for first and second cardiac regions over one cardiac cycle based on cardiac wall motion contours. First and second regional displacement curves are generated based on the regional displacement magnitudes calculated for the first and second cardiac regions, respectively. A common magnitude reference is provided to the first and second regional displacement curves. The first and second regional displacement curves are each averaged over a predetermined number of cardiac cycles, and then smoothed. A relative phase representing a phase relationship between the first and second regional displacement curves is computed based on a frequency analysis. The relative phase indicates a degree of cardiac wall motion asynchrony reflected in the echocardiogram.

In one embodiment, a sequence of therapies is delivered. An echocardiogram is recorded during the delivery of the sequence of therapies. Degrees of ventricular asynchrony, each associated with one therapy of the sequence of therapies, are computed based the echocardiogram. An approximately optimal therapy is then determined based on the degrees of ventricular asynchrony.

This summary is intended not to limit the claimed subject matter, and the scope of the invention is defined by attached claims and their equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, an echocardiographic analysis method and apparatus in applications involving cardiac rhythm management systems treating heart failure by delivering CRT. However, it is to be understood that the present method and apparatus of echocardiographic analysis may be generally employed in evaluation and/or management of heart conditions that involve quantification of cardiac wall motion.

Studies using multiple gated equilibrium blood pool scintigraphy demonstrated reduced interventricular phase shifts between the LV and RV contraction sequence with CRT, but came to conflicting conclusions about whether CRT reduced intraventricular asynchrony. Tagged magnetic resonance imaging has been used to quantify baseline intraventricular mechanical dyssynchrony, but is not applicable to patients with implanted pacemakers. In contrast, echocardiography is a widely available imaging modality for rapid bedside evaluation of cardiac function and ventricular wall motion abnormalities. Abnormal septal wall motion patterns in patients with bundle-branch block and ventricular pacing have been studied by M-Mode echocardiography, but these measurements are limited to the evaluation of radial function in the basal LV segments using the parastemal views. Improvement of LV asynchrony was quantified with tissue Doppler imaging from the apical views, but this technique is limited to the study of longitudinal axis motion. Two-dimensional Fourier phase imaging may be able to quantify wall motion asynchrony in the radial direction and has been used to assess LV asynergy in coronary artery disease (CAD).

One embodiment of the present method and apparatus uses a phase analysis technique to quantify regional wall motion asynchrony from endocardial border contours generated from 2-dimensional echocardiographic ventricular images. In one embodiment, the phase analysis technique is used to predict the magnitude of contractile function improvement with CRT by quantifying a degree of radial ventricular asynchrony in heart failure patients with ventricular conduction delay.

Figure 1:
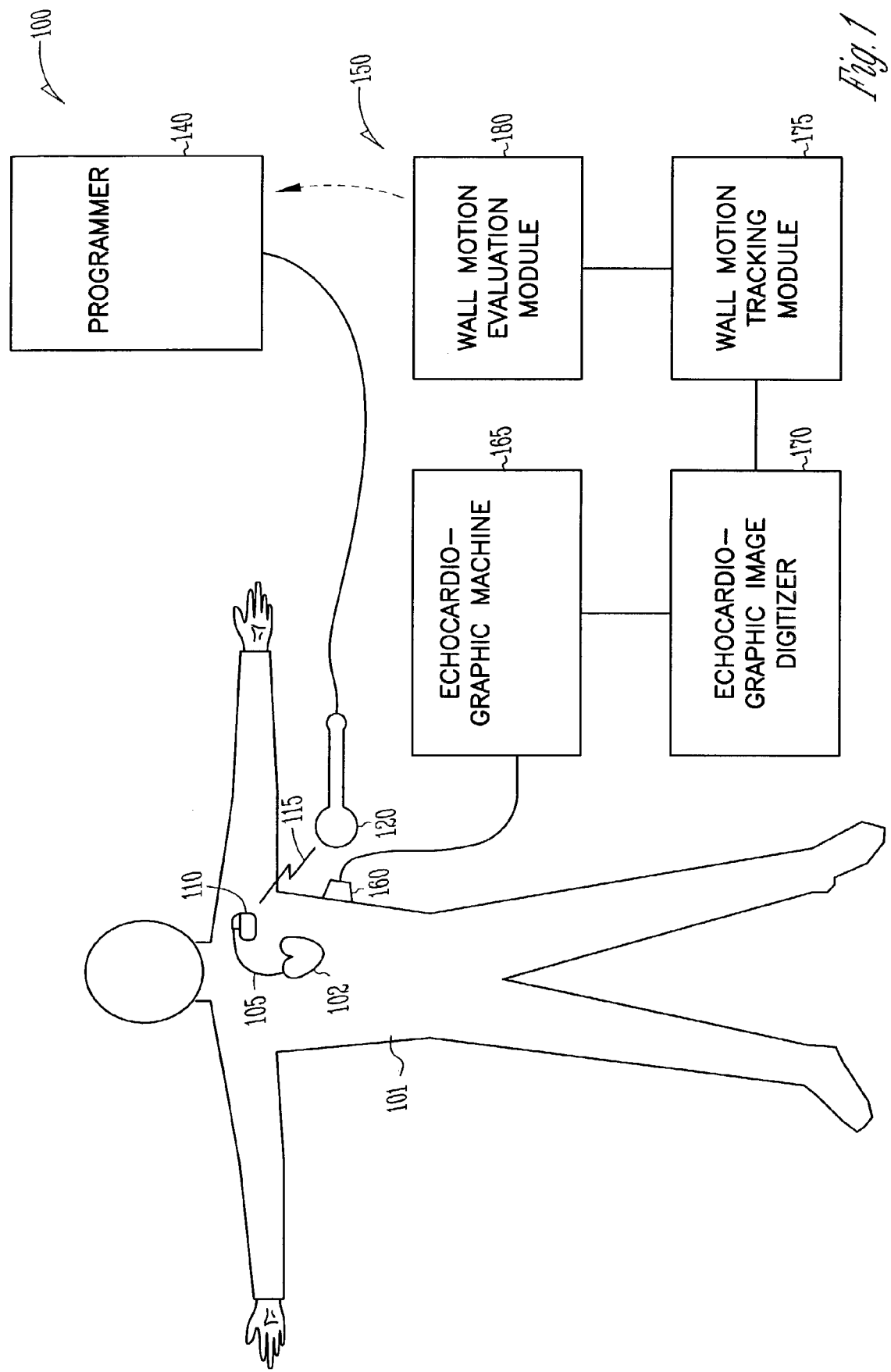
FIG. 1 is a schematic/block diagram illustrating one embodiment of portions of a cardiac rhythm management system and portions of an echocardiographic analysis system performing echocardiographic quantification of ventricular asynchrony.

FIG. 1 is a schematic/block diagram illustrating one embodiment of portions of a cardiac rhythm management system 100 and portions of an echocardiographic analysis system 150 performing echocardiographic quantification of ventricular asynchrony. In one embodiment, system 100 includes, among other things, an implanted device 110 and an external programmer 140. Implanted device 110 is implanted within a patient's body 101 and coupled to the patient's heart 102 by a lead system 105. Examples of implanted device 110 include CRT devices, pacemakers, cardioverter/defibrillators, pacemaker/defibrillators, and drug delivery devices. Programmer 140 provides a user interface for system 100. The user interface allows a physician or other caregiver to interact with implanted device 110 through a telemetry link 115.

In one embodiment, as illustrated in FIG. 1, telemetry link 115 is an inductive telemetry link supported by a mutual inductance between two closely-placed coils, one housed in a wand 120 near or attached onto body 101 and the other housed in implanted device 110. In an alternative embodiment, telemetry link 115 is a far-field telemetry link. In one embodiment, telemetry link 115 provides for data transmission from implanted device 110 to programmer 140. This may include, for example, transmitting real-time physiological data acquired by implanted device 110, extracting physiological data acquired by and stored in implanted device 110, extracting therapy history data stored in implanted device 110, and extracting data indicating an operational status of implanted device 110 (e.g., battery status and lead impedance). In a further embodiment, telemetry link 115 provides for data transmission from programmer 140 to implanted device 110. This may include, for example, programming implanted device 110 to acquire physiological data, programming implanted device 110 to perform at least one self-diagnostic test (such as for a device operational status), and programming implanted device 110 to deliver at least one therapy.

In one embodiment, programming implanted device 110 includes sending therapy parameters to implantable device 110. In one embodiment, the therapy parameters are selected to provide an approximately optimal hemodynamic performance of a patient by delivering cardiac pacing pulses to the patient's heart. In this embodiment, there is a need to predict whether the patient will benefit from selected therapy mode and parameters. It was learned that such a need could be met by quantifying cardiac wall motion based on echocardiographic images. In one embodiment, as illustrated in FIG. 1, an echocardiographic analysis system 150 provides for echocardiographic quantification of intraventricular asynchrony. In one specific embodiment, the echocardiographic quantification of intraventricular asynchrony is performed to evaluate benefits of CRT in patients having heart failure and abnormal conduction delay.

In one embodiment, as illustrated in FIG. 1, echocardiographic analysis system 150 includes an echocardiographic sensor 160, an echocardiographic machine 165, an echocardiographic image digitizer 170, a wall motion tracking module 175, and a wall motion evaluation module 180. In one embodiment, echocardiographic sensor 160 and echocardiographic machine 165 are commercial devices providing echocardiogram showing radial ventricular wall motion. In one embodiment, the echocardiogram is recorded on a storage medium such as a videotape. Echocardiographic image digitizer 170 digitizes the recorded echocardiogram in a sequence of echocardiographic image frames. Wall motion tracking module 175 detects endocardial border contours from each echocardiographic image frame of the digitized echocardiogram. In one embodiment, wall motion tracking module 175 includes portions of a commercial echocardiographic analysis system (for example, Echo-CMS [Echocardiographic Measurement Systreml], version 2.2, by Medis, Leiden, Netherlands). Medis Echo-CMS includes a border detection software allowing detection of endocardial border contours from each echocardiographic image frame of the digitized echocardiogram. In one embodiment, wall motion evaluation module 180 performs an echocardiographic phase analysis for quantification of LV regional wall motion asynchrony from the endocardial border contours. Wall motion evaluation module 180 is further discussed below with reference to FIG. 4. In one embodiment, result of the quantification of LV regional wall motion asynchrony is used to predict potential benefits of a CRT pacing therapy. In one embodiment, the result is used to determine whether the CRT pacing therapy should be used. In a further embodiment, the result provides for a basis for selecting a pacing mode, one or more pacing sites, and/or one or more pacing parameters (such as atrioventricular delays) providing for an approximately highest degree of LV synchrony for patients with heart failure and abnormal conduction delay such as LBBB.

Figure 2:
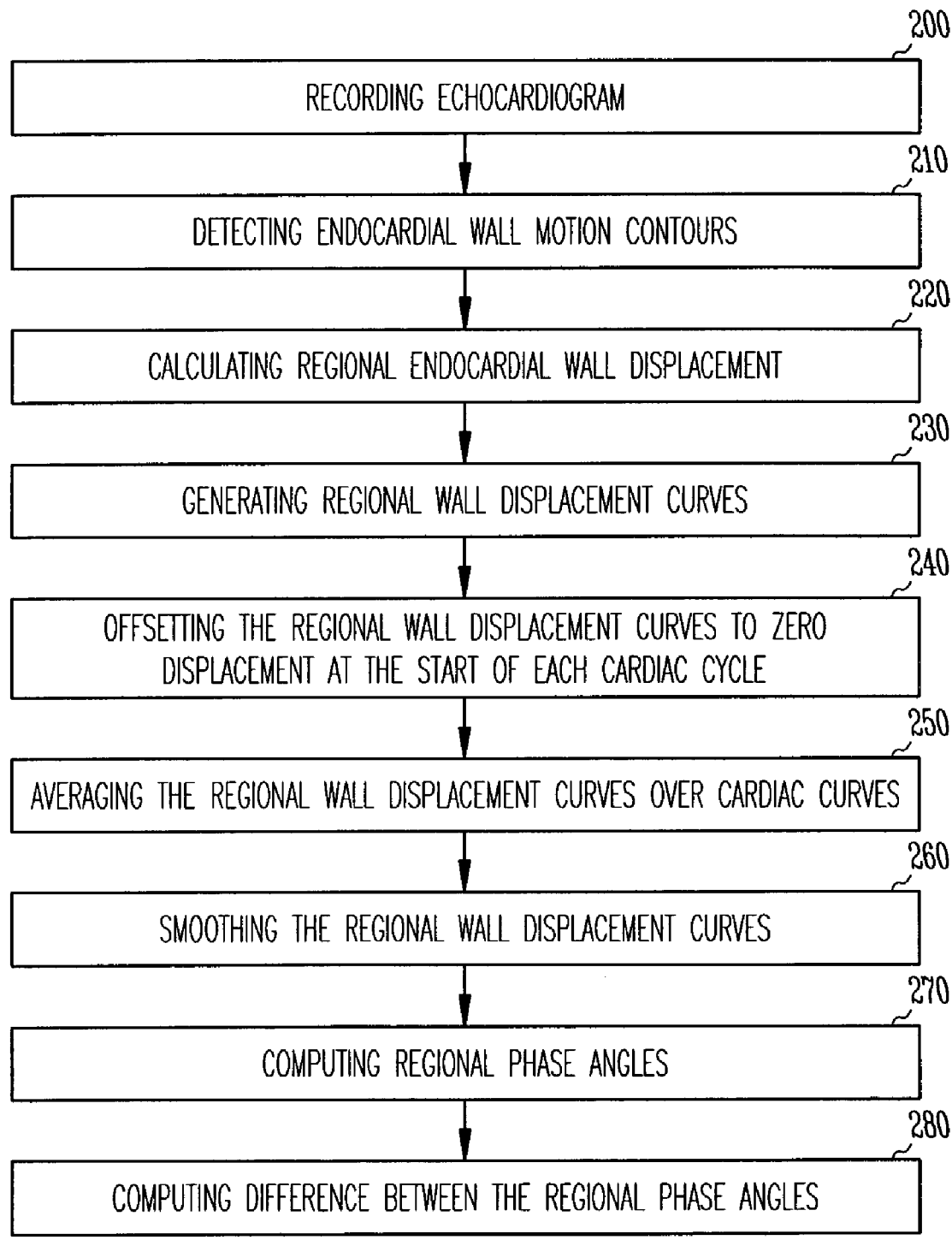
FIG. 2 is a flow chart illustrating one embodiment of a method of echocardiographic quantification of ventricular asynchrony using the echocardiographic analysis system.

FIG. 2 is a flow chart illustrating one embodiment of a method of echocardiographic quantification of ventricular asynchrony using echocardiographic analysis system 150. At 200, transthoracic echocardiogram is recorded by using echocardiographic sensor 160 and echocardiography machine 165. The orientation of echocardiographic sensor 160 relative to a patient depends on the plane on which the ventricular wall motion is of interest. The echocardiogram provides sufficient image quality with complete endocardial border delineation. In one embodiment, the echocardiogram is recorded with a patient lying in the left lateral supine position at rest. In one embodiment, to minimize influence of relative motion of the heart, only portions of the echocardiogram obtained during respiratory hold and with a stable transducer position are included in the quantification of ventricular asynchrony. In one embodiment, the echocardiogram is recorded to provide a "baseline," where no cardiac therapy is being delivered. In another embodiment, the echocardiogram is recorded while a cardiac therapy is being delivered to evaluate the therapy. In a specific embodiment, the cardiac therapy is a CRT pacing therapy. In one embodiment, the echocardiogram is recorded and stored on a storage medium. In one specific embodiment, the storage medium is a videotape. In one embodiment, the echocardiogram is digitized into sequential echocardiographic image frames for wall motion analysis with the Medis Echo-CMS.

During a cardiac cycle, each region of the ventricular endocardial wall undergoes a cycle of inward and outward displacement. Each regional displacement cycle can be represented by a regional displacement curve that includes displacement magnitude plotted over time from the start to the end of a cardiac cycle interval. Because these displacement curves are periodic, they can be analyzed in the frequency domain to quantify the phase relationship between curves independent of the displacement magnitude and heart rate. Each regional displacement curve is modeled as a wave with period equal to the cardiac cycle interval, which is used as the fundamental frequency in a Fourier analysis. The time at which the center of this wave occurs during the cardiac cycle interval is a function of the fundamental frequency phase angle ($\Phi$). It is near 180° when centered in the middle of the cycle, 0–180° if it is shifted earlier, and 180–360° if it is shifted later. Inverted and triphasic displacement curves (e.g., with paradoxical septal wall motion) have phase angles near the end (360°) or start (0°) of the cycle. With this method, a degree of asynchrony between two regional displacement curves is represented by the difference between their respective phase angles. Phase differences near 0° indicate near-perfect synchrony, while a difference of 180° defines maximal asynchrony. A method for computing the phase angle difference between two regional displacement curves is discussed as follows.

Figure 3A:
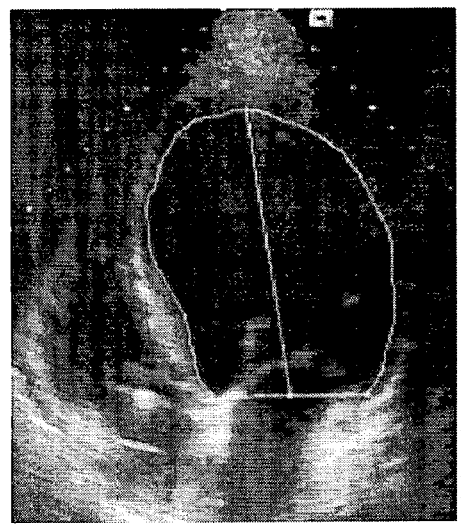
FIG. 3A is an illustration of an example of an echocardiographic image with an endocardial LV wall contour indicated.

At 210, ventricular endocardial wall motion is delineated and tracked in the sequential echocardiographic image frames of the digitized echocardiogram. In one embodiment, the Medis Echo-CMS border detection software is used to delineate and track the LV endocardial wall motion in the sequential echocardiographic image frames of a digitized apical 4-chamber view echocardiogram. In one embodiment, end-diastole is demarcated by the frame in which the mitral valve first begins to close, and end-systole is demarcated by the frame in which the mitral valve first begins to open. Wall motion contours, such as the one illustrated in FIG. 3A, are manually drawn in the first systolic and diastolic frames of each cardiac cycle, and the Medis Echo-CMS border detection software automatically generates intermediate frame contours, which are manually adjusted as necessary. In one embodiment, each endocardial motion is tracked through 3–7 cardiac cycles in normal sinus rhythm. In one embodiment, normal sinus rhythm is verified by a concurrent surface electrocardiographic (ECG) recording.

Figure 3B:
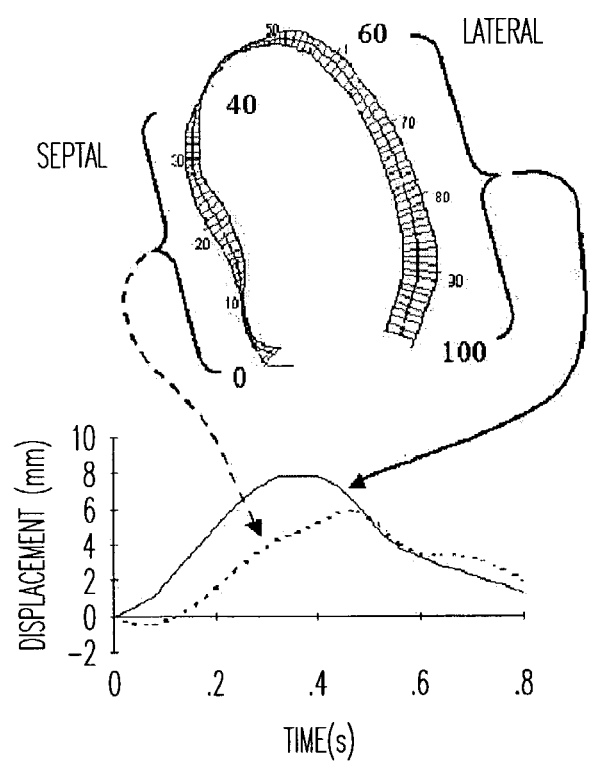
FIG. 3B is an illustration of an example of LV regional wall displacement segments calculated from the endocardial LV wall contours over a cardiac cycle and LV regional wall displacement curves over the cardiac cycle.

At 220, regional endocardial displacement is calculated for each cardiac cycle. In one embodiment, the Medis Echo-CMS software automatically calculates regional endocardial displacement magnitudes using a centerline method for 100 equally spaced segments on the LV wall motion contours, as illustrated in FIG. 3B. This method has been shown to reduce interobserver variability in the delineation of endocardial boundaries.

At 230, regional endocardial displacement curves are generated based on the regional endocardial displacement magnitudes. The number of the regional endocardial displacement curves to be generated depends on the desirable resolution in locating cardiac regions where abnormal electrical conduction or muscular excitation occurs. In one embodiment, septal and lateral wall displacement curves are calculated based on regional endocardial displacement magnitudes for selected segments on the LV wall motion contours that indicate septal and lateral wall motion, respectively. In one embodiment, as illustrated in FIG. 3B, 40 segments from the basal septum toward the apex and 40 segments from the basal lateral wall toward the apex are averaged for calculation of the septal and lateral regional displacement curves, respectively. At 240, the regional displacement curves are each offset to a common magnitude reference point. In one specific embodiment, the septal and lateral wall displacement curves are each offset to zero displacement at the start of each cardiac cycle. In one embodiment, the regional displacement curves are each averaged over several cardiac cycles at 250. In a specific embodiment, the septal and lateral wall displacement curves are averaged over 3–7 cardiac cycles using the first systolic frame as a fiducial marker for the start of each cardiac cycle. In one embodiment, the averaged regional displacement curves are smoothed at 260. In one specific embodiment, the septal and lateral wall displacement curves are smoothed with a three-frame moving average filter.

At 270, regional displacement phases corresponding to the regional displacement curves are computed. The regional displacement phases are defined as regional phase angles. In one specific embodiment, septal and lateral displacement phases are defined by computing their respective phase angles, $\Phi_S$ and $\Phi_L$. In one embodiment, each regional phase angle, $\Phi$, is the phase angle of the fundamental frequency of a Fourier transform computed over the corresponding regional displacement curve ($\overline{D}$):

$$\Phi = \tan^{-1} \frac{\langle \overline{D}, \sin \rangle}{\langle \overline{D}, \cos \rangle}.$$

Phase angle $\Phi$ is computed with the discrete frame data using the inner product of the regional displacement curve and orthogonal sine and cosine curves of cardiac cycle interval length. In one embodiment, septal wall displacement curves exhibiting paradoxical outward displacement during systole that yield a very small phase angle (<60°) due to the 360° modulus are adjusted to (360°−$\Phi_S$).

At 280, differences between the regional phase angles are computed to quantify a degree of asynchrony with respect to the corresponding regional wall motions. In one specific embodiment, lateral and septal phase relationships are measured by the difference between the lateral phase angle $\Phi_L$ and septal phase angle $\Phi_S$: $\Phi_{LS} = \Phi_L - \Phi_S$. In one embodiment, the absolute value of $\Phi_{LS}$, $|\Phi_{LS}| = |\Phi_L - \Phi_S|$, represents the degree of the ventricular wall motion asynchrony. In one specific embodiment, where $\Phi_L$ and $\Phi_S$ represent LV lateral and septal phase angles, respectively, $|\Phi_{LS}|$ quantifies LV asynchrony in patients with heart failure and abnormal conduction delay such as LBBB.

Figure 4:
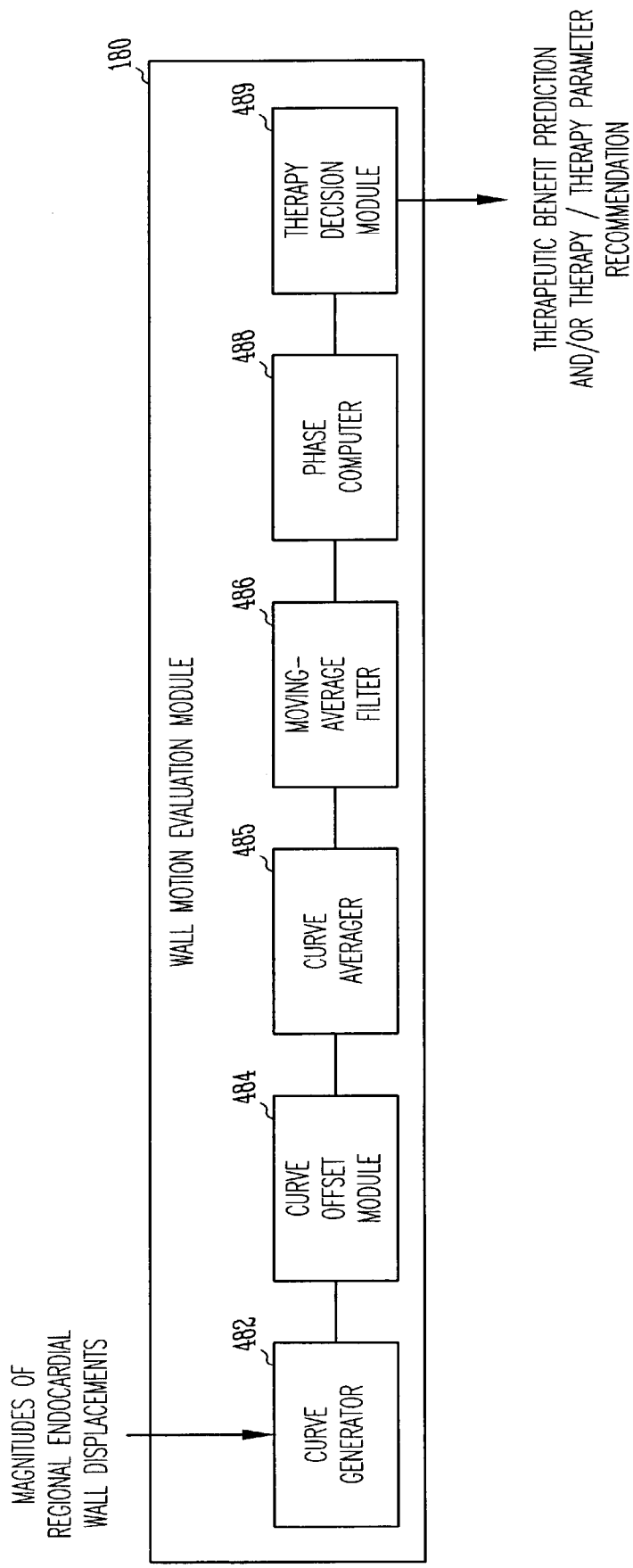
FIG. 4 is a schematic/block diagram illustrating one embodiment of portions of a wall motion evaluation module of the echocardiographic analysis system.

FIG. 4 is a schematic/block diagram illustrating one embodiment of portions of wall motion evaluation module 180 of echocardiographic analysis system 150. In the embodiment of FIG. 2, commercial echocardiographic sensor and machine are used to record an echocardiogram, the Medis Echo-CMS border detection software performs steps 210 and 220, and wall motion evaluation module 180 performs steps 230–280. In one embodiment, portions of wall motion evaluation module 180 are implemented as software. In one further embodiment, wall motion evaluation module 180 includes software designed to run on a computer. In one embodiment, portions of wall motion evaluation module 180 are implemented as hardware. In one embodiment, portions of wall motion evaluation module 180 are implemented as firmware. In one embodiment, wall motion evaluation module 180 is implemented as a combination of two or more of software, hardware, and firmware. In one embodiment, wall motion evaluation module 180 includes a curve generator 482, a curve offset module 484, a curve averager 485, a moving-average filter 486, a phase computer 488, and a therapy decision module 489.

Curve generator 482 generates the regional wall displacement curves. In one embodiment, curve generator 482 calculates the septal and lateral wall displacement curves based on the regional endocardial displacement magnitude for the selected segments on the LV wall motion contours that indicate septal and lateral wall motions, respectively. In one specific embodiment, curve generator 482 calculates the septal and lateral wall displacement curves by averaging the 40 segments from the basal septum toward the apex and 40 segments from the basal lateral wall toward the apex, as illustrated in FIG. 3B. Curve offset module 484 applies an offset to each of the regional displacement curves to provide for a common reference for the regional displacement magnitudes. In one specific embodiment, curve offset module 484 applies an offset to each of the septal and lateral wall displacement curves such that the curves are each offset to zero displacement at the start of each cardiac cycle. Curve averager 485 averages each of the regional wall displacement curves over several cardiac cycles. In one specific embodiment, curve averager 485 averages each of the septal and lateral wall displacement curves over 3–7 cardiac cycles using the first systolic frame as the fiducial marker for the start of each cardiac cycle. In one embodiment, moving-average filter 486 smoothes the averaged regional displacement curves over several sequential echocardiographic image frames. In a specific embodiment, moving-average filter 486 smoothes the averaged septal and lateral wall displacement curves by moving-averaging three sequential echocardiographic image frames.

Phase computer 488 includes a regional displacement phase calculator that calculates regional displacement phase angles corresponding to the regional displacement curves. In one embodiment, the regional displacement phase calculator includes a septal wall displacement phase calculator and a lateral wall displacement phase calculator to calculate the septal and lateral displacement phase angles $\Phi_S$ and $\Phi_L$, respectively. In one embodiment, the regional displacement phase calculator includes a Fourier analysis module to compute a Fourier transform over each of the regional displacement curve. In one specific embodiment, the regional displacement phase calculator calculates phase angle $\Phi$ over a regional displacement curve ($\overline{D}$):

$$\Phi = \tan^{-1} \frac{\langle \overline{D}, \sin \rangle}{\langle \overline{D}, \cos \rangle}.$$

The regional displacement phase calculator calculates $\Phi$ with the discrete frame data using the inner product of the regional displacement curve and orthogonal sine and cosine curves of cardiac cycle interval length. Septal wall displacement curves exhibiting paradoxical negative displacement during systole that yielded a very small phase angle (<60°) due to the 360° modulus are adjusted to (360°−$\Phi_S$).

Phase computer 488 further includes a relative phase calculator that calculates differences between the regional phase angles. In one embodiment, the relative phase calculator calculates a difference between the lateral phase angle $\Phi_L$ and septal phase angle $\Phi_S$: $\Phi_{LS}=\Phi_L-\Phi_S$. In one embodiment, the relative phase calculator calculates the absolute value of $\Phi_{LS}$, $|\Phi_{LS}|=|\Phi_L-\Phi_S|$, which represents the degree of the ventricular wall motion asynchrony. In one specific embodiment, where $\Phi_L$ and $\Phi_S$ represent LV lateral and septal phase angles, respectively, the relative phase calculator calculates $|\Phi_{LS}|$ to quantify LV asynchrony in patients with heart failure and abnormal conduction delay such as LBBB.

Therapy decision module 489 predicts whether a patient will likely benefit from a therapy and/or recommends a particular therapy or therapy parameter(s) based on one or more of $\Phi_L$, $\Phi_S$, $\Phi_{LS}$, and $|\Phi_{LS}|$. In one embodiment, therapy decision module 489 includes a therapy decision comparator that compares $|\Phi_{LS}|$ to a predetermined threshold. In one specific embodiment, therapy decision module 489 predicts that a patient will likely benefit from CRT when $|\Phi_{LS}|$ exceeds the predetermined threshold. The threshold represents a degree of ventricular wall motion asynchrony that is expected to be reduced by CRT. In one specific embodiment, the threshold is 25 degrees. In another embodiment, therapy decision module 489 recommends one or one set of approximately optimal therapy parameters based on one or more of $\Phi_L$, $\Phi_S$, $\Phi_{LS}$, and $|\Phi_{LS}|$ computed from regional endocardial wall displacements measured while a sequence of therapies are delivered for evaluation. In one specific embodiment, the one or one set of approximately optimal therapy parameters are selected from the parameters defining the sequence of therapies. When the therapy is a CRT pacing therapy, the approximately optimal therapy parameters include, but is not limited to, one or more of pacing sites and timing for pacing pulse delivery to each pacing site, such as atrioventricular delays (AVDs) and interventricular delays.

Figure 5:
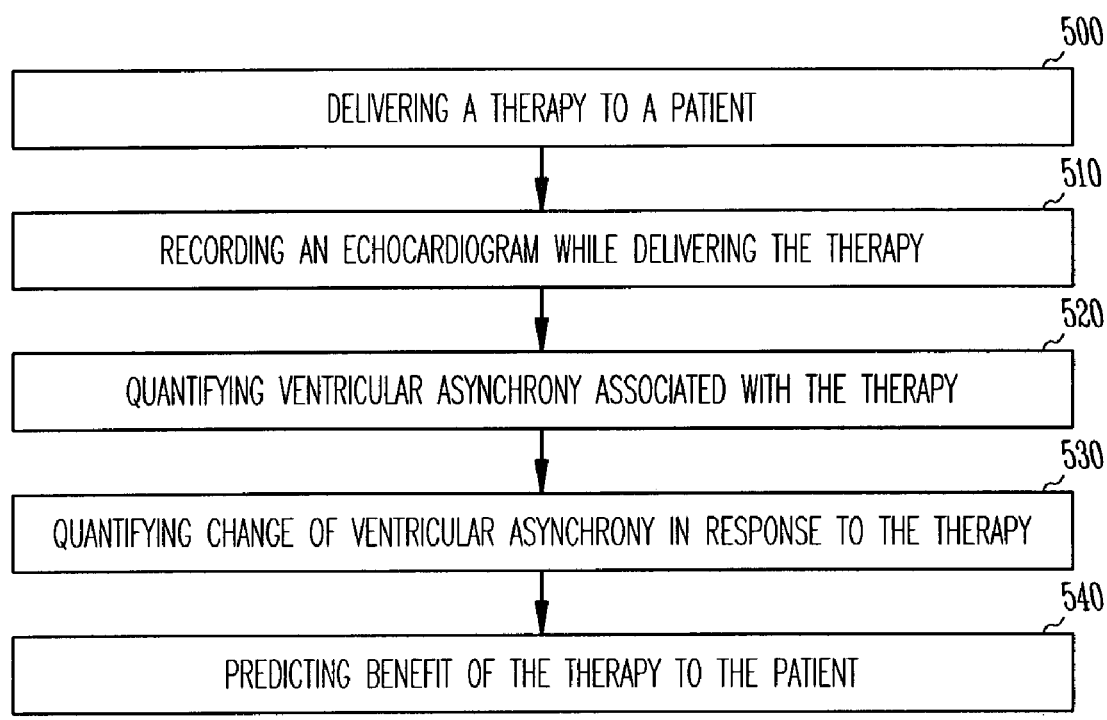
FIG. 5 is a flow chart illustrating one embodiment of a method for identifying therapy candidates based on the echocardiographic quantification of ventricular asynchrony.

FIG. 5 is a flow chart illustrating one embodiment of a method for identifying therapy candidates based on the echocardiographic quantification of ventricular asynchrony using echocardiographic analysis system 150. Patients having abnormal heart conditions are evaluated to determine whether a cardiac therapy such as CRT will be effective in improving each patient's intraventricular wall motion synchrony. At 500, a cardiac therapy is delivered to a patient. In one embodiment, the therapy is a CRT pacing therapy. An echocardiogram is recorded at 510, while the cardiac therapy is delivered. In one embodiment, the echocardiogram includes portions recorded while the cardiac therapy is being delivered and portions recorded when no cardiac therapy is being delivered. At 520, the patient's response to the delivery of the cardiac therapy is evaluated by quantifying the patient's ventricular asynchrony associated with the therapy by analyzing the echocardiogram recorded during the delivery of the therapy. In one embodiment, the method discussed with reference to FIG. 2, including steps 200–280, is incorporated into step 520. At 530, the effect of delivering the cardiac therapy to the patient is evaluated. This includes quantifying a change of ventricular asynchrony in response to the delivery of the cardiac therapy. In one embodiment, quantifying the change of ventricular asynchrony in response to the delivery of the cardiac therapy includes comparing the degree of the patient's ventricular asynchrony associated with the cardiac therapy with the degree of the patient's ventricular asynchrony associated with non-therapy. In one specific embodiment, this includes comparing the value of $\Phi_{LS}$ associated with the cardiac therapy with the value of $\Phi_{LS}$ associated with non-therapy. In one embodiment, the patient's ventricular asynchrony associated with non-therapy is quantified using the method discussed with reference to FIG. 2, including steps 200–280, with a echocardiogram being recorded when no cardiac therapy is being delivered. In another embodiment, the patient's ventricular asynchrony associated with non-therapy is quantified using the method discussed with reference to FIG. 2, including steps 200–280, with the portions of the echocardiogram being recorded when no cardiac therapy is being delivered. In one specific embodiment, quantifying the change of ventricular asynchrony includes quantifying a reduction of ventricular asynchrony in response to the delivery of the cardiac therapy. At 540, benefit of the cardiac therapy to the patient is predicted based on the difference between the degree of the patient's ventricular asynchrony associated with the cardiac therapy and the degree of the patient's ventricular asynchrony associated with non-therapy. In one specific embodiment, a patient is predicted to benefit from the cardiac therapy if the value of $\Phi_{LS}$ is reduced by the cardiac therapy. In a further embodiment, the magnitude of the benefit of the cardiac therapy to the patient is indicated by the difference between the value of $\Phi_{LS}$ associated with the cardiac therapy and the value of $\Phi_{LS}$ associated with non-therapy.

A Study Using Echocardiographic Quantification of LV Asynchrony

The following portions of this document discusses, by way of example, but not by way of limitation, a study including selected embodiments of the method and apparatus discussed above with reference to FIGS. 1–4. The study was performed to test a hypothesis that the degree of radial ventricular asynchrony in patients with heart failure with a ventricular conduction delay predicts the magnitude of contractile function improvement with CRT.

Methods of the Study

Patients. The study, known as the Pacing Therapies in Congestive Heart Failure (PATH-CHF) trial, is a prospective multicenter single-blinded cross-over study and included 42 patients with dilated cardiomyopathy irrespective of ischemic (coronary artery disease [CAD]) or non-ischemic (dilated cardiomyopathy [DCM]) etiology, QRS width>120 ms and PR interval>150 ms. All patients were in stable New York Heart Association (NYHA) class III heart failure without change in medication or in NYHA class IV without need for intravenous inotropic drugs during the last month in order to be eligible for the study. All patients received an implantable CRT system including two pacemakers to deliver RV, LV, or biventricular (BV) CRT including, respectively, RV, LV, or BV pacing in VDD mode. Echocardiographic results obtained in the patient group were compared to a control group of 10 healthy individuals with normal PR interval and QRS width.

Invasive optimization. During implantation, invasive hemodynamic testing was performed with repeated measurement of $dP/dt_{max}$ at various atrioventricular (AV) delays and pacing sites (RV, LV and BV) tested in random order in VDD mode. Response to pacing was expressed as percent increase in $dP/dt_{max}$ (% $\Delta dP/dt_{max}$) compared with no pacing. Evaluation of invasive parameters was performed blinded to the echocardiographic analysis.

Echocardiographic analysis. For baseline evaluation, transthoracic echocardiograms of 34 patients were analyzed if there was sufficient image quality for complete endocardial border delineation. Studies were recorded with the patient lying in the left lateral supine position at rest in the week prior to implantation of the CRT system. To minimize influence of relative motion of the heart, only echocardiographic recordings that were obtained in respiratory hold and with a stable transducer position were included. Fundamental imaging was used in the majority of baseline examinations (n=26); harmonic imaging was used whenever it was available to the study center (n=8). At the first follow-up visit, 4 weeks after implantation, echocardiographic recordings were made with acute reprogramming of the CRT system to no pacing (OFF) and to RV, LV, and BV VDD pacing in random order. For each individual, the AV delay was programmed close to the optimal setting as determined by the invasive hemodynamic testing during implantation and kept constant for each pacing mode. Valid echocardiographic images from the 4-week follow-up were available for analysis in 16 patients. Two patients were excluded from the study due to high pacing thresholds, two patients had sudden cardiac death, and 14 patients were excluded because they had technically inadequate echocardiographic recordings in at least one tested pacing mode. All examinations were recorded and stored on S-VHS videotape and later digitized for wall motion analysis with the Medis Echo-CMS at the responsible core-center (University Hospital, Aachen, Germany).

Quantification of ventricular asynchrony. All wall motion analyses were performed blinded to the invasive hemodynamic test results and clinical patient characteristics. The pacing mode was marked on videotape for identification. A semiautomatic border detection software included in the Medis Echo-CMS echo analysis system ("the CMS software") was used to delineate and track the LV endocardial wall motion in sequential frames of digitized images from an apical 4-chamber view. End-diastole was demarcated by the frame in which the mitral valve first began to close; end-systole was demarcated by the frame in which the mitral valve first began to open. Wall motion contours (FIG. 3A) were manually drawn in the first systolic and diastolic frames of each cardiac cycle, and the CMS software automatically generated intermediate frame contours, which were manually adjusted as necessary. For each CRT mode, endocardial motion was tracked through 3–7 cardiac cycles verified to be in normal sinus rhythm by concurrent surface ECG recording. Regional endocardial displacement was calculated for each cardiac cycle automatically by the CMS software using the centerline method for 100 equally spaced segments on the LV wall motion contours (FIG. 3B). This method has been shown to reduce interobserver variability in the delineation of endocardial boundaries.

Forty segments from the basal septum toward the apex and 40 segments from the basal lateral wall toward the apex were averaged for calculation of septal and lateral regional displacement curves (FIG. 3B). Regional displacement curves were together averaged over 3–7 cardiac cycles using the first systolic frame as the fiducial marker. Each curve was offset to zero displacement at the start of each cycle. Before phase analysis, the average regional displacement curves were smoothed with a three-frame moving average filter. Septal and lateral displacement phases were defined by the phase angle of the fundamental frequency of the Fourier transform computed over the cardiac cycle regional displacement curve ($\overline{D}$):

$$\Phi = \tan^{-1} \frac{\langle \overline{D}, \sin \rangle}{\langle \overline{D}, \cos \rangle}.$$

This phase angle was computed with the discrete frame data using the inner product of the regional displacement curve and orthogonal sine and cosine curves of cardiac cycle interval length. Septal displacement curves exhibiting paradoxical negative displacement during systole that yielded a very small phase angle (<60°) due to the 360° modulus were adjusted to (360°−$\Phi_S$). Lateral (L) and septal (S) phase relationships were measured by the difference between the lateral ($\Phi_L$) and septal ($\Phi_S$) phase angles: $\Phi_{LS}=\Phi=\Phi_S$. The absolute value of $\Phi_{LS}$ was used as an order-independent measure of synchrony: $|\Phi_{LS}|=|\Phi_L-\Phi_S|$.

Statistics. Continuous data are expressed in the text as the mean value ± standard deviation (SD). To evaluate and compare the effects of RV, LV, and BV pacing and no-pacing treatments on hemodynamic and echocardiographic measurements from each individual, a general linear model (analysis of variance [ANOVA]) accounting for all treatment variations being tested in each patient was used. To compare measurements among control and L-S phase type groups, independent samples ANOVA was used. For both ANOVAs, the Tukey correction was used to correct for Type I error inflation introduced by testing multiple hypotheses. An unpaired t-test was used to compare characteristics of analyzed and excluded patient groups and to compare measurements from DCM and CAD patients. Statistical analyses were made with SAS (version 8.2, SAS Institute, Cary, N.C.). Reproducibility of endocardial border delineation and phase angle analysis was assessed in 10 randomly selected baseline examinations as the mean difference between two independent measurements performed on different occasions by one observer (intra-observer variability) and between two independent observers (interobserver variability). The results were expressed as percentages of the first measurement (±SD) and in addition as percentages of 180° (±SD), based on the fact that two measurements cannot differ by more than 180° over the 360° cycle.

Results of the Study

At baseline, the 34 patients (mean age 59±6 years; 19 men and 15 women) presented, in the majority of cases, with NYHA functional class III (n=33), LBBB (n=32) and nonischemic DCM (n=24). The mean QRS width was 176±34 ms; the mean PR interval was 211±38 ms; and the LV ejection fraction was significantly reduced (mean 21±6%). The mean % $\Delta dP/dt_{max}$ with optimized CRT during invasive testing was 7.6±7.7% with RV pacing, 19.2±15.6% (p<0.001 vs. RV) with LV pacing and 17.8±14.5% (p<0.001 vs. RV) with BV pacing. The mean intrinsic AV interval for the patient sample was 221±38ms and the average programmed AV interval during follow-up CRT testing and echocardiographic recording was 107±28ms. All individuals in the control group presented with a normal echocardiographic LV ejection fraction of more than 60%. The 16 patients studied at the first follow-up after 4 weeks was comparable to the 18 excluded patients in terms of age (59±6 years vs. 60±6 years, p=NS), baseline QRS (172±32 ms vs. 179±36 ins, p=NS), $|\Phi_{LS}|$(82±37° vs. 87±54°), baseline $dP/dt_{max}$ (600±161 mmHg vs. 527±83 mmHg, p=NS) and % $\Delta dP/dt_{max}$ (21±14% vs.19±17%, p=NS). All patients were receiving stable pharmacological therapy from baseline to 4-weeks follow-up, except one patient who began beta-blocker therapy just before the 4-week follow-up.

Baseline lateral-septal (L-S) phase relationships. FIGS. 6A–D include examples of the control and types 1–3 wall motion patterns. In FIGS. 6A–D, consecutive cardiac cycles are averaged to show wall motion for lateral (solid line) and septal (dashed line) segments as displacement over time.

Figure 6A:
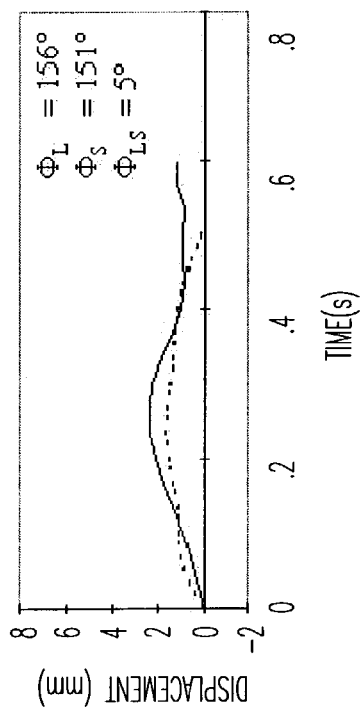
FIGS. 6A–D are illustrations of exemplary average septal-lateral wall displacement curves for different type wall motion patterns.
Figure 6B:
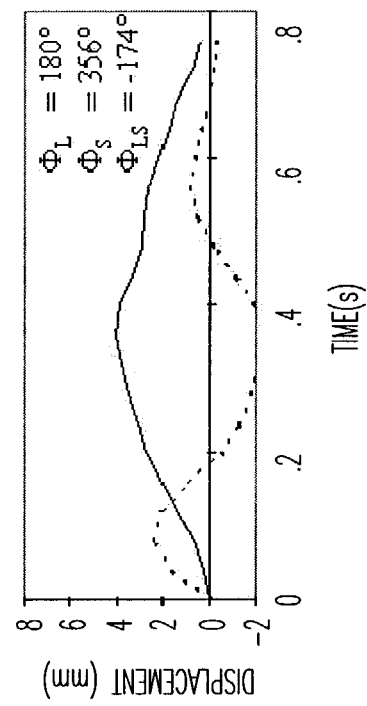
Figure 6C:
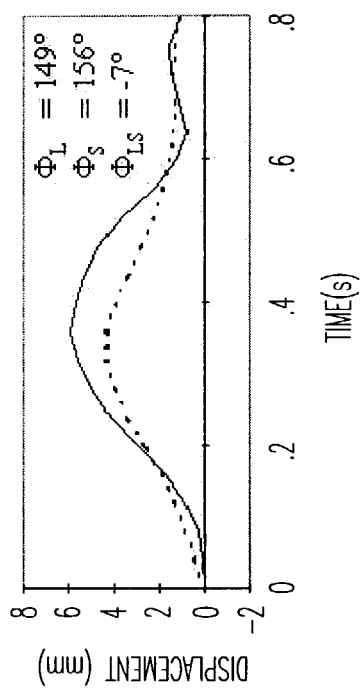
Figure 6D:
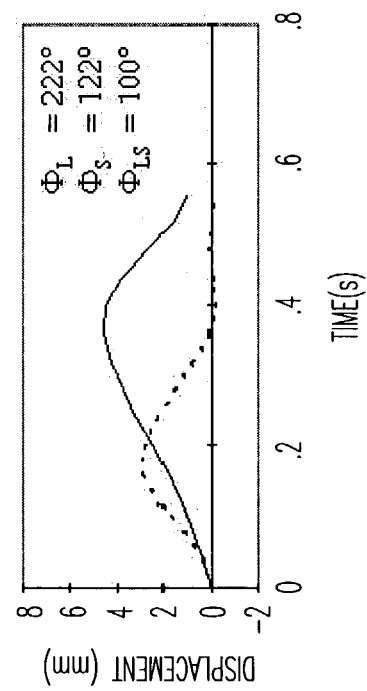

All control subjects were characterized by monophasic lateral and septal displacements with $|\Phi_{LS}|<25°$, which are defined as near-synchronous phase (e.g., FIG. 6A). Three distinct types of L-S phase relationships were retrospectively identified in the 34 patients analyzed at baseline. A type 1 pattern, similar to the observed pattern in the control population, was apparent in 4 patients and was characterized by monophasic lateral and septal displacements with $|\Phi_{LS}|<25°$ (mean $\Phi_{LS}$5±6°, e.g., FIG. 6B). A type 2 pattern was defined by a septal phase preceding the lateral phase by more than 25° with either monophasic or biphasic septal displacements (e.g., FIG. 6C), which was observed in 17 patients (mean $\Phi_{LS}$77±33°). Thirteen patients showed a type 3 pattern (mean $\Phi_{LS}$-115±33°) with a late septal phase (e.g., FIG. 6D). This pattern was usually associated with a triphasic or inverted monophasic septal displacement.

Table 1 summarizes the distribution of L-S phase types and the corresponding patient characteristics. The baseline $dP/dt_{max}$ tended to be highest and the QRS duration shortest in type 1 patients, and this groun showed least benefit from pacing as measured by mean % $\Delta dP/dt_{max}$ with CRT. Table 2 compares the non-invasive measures for LV asynchrony (QRS width and $\Phi_{LS}$) with the individual hemodynamic response to CRT. None of the four type 1 patients had improved $dP/dt_{max}$ with CRT, even though one had a QRS of 153 ms and baseline $dP/dt_{max}<500$ mmHg/s (patient no. 4). In contrast, even though two type 2 patients had QRS≦130 ms (patients nos. 5–6), ventricular pre-excitation due to BV CRT led to 11% to 17% increases in $dP/dt_{max}$. Three patients did not have improved $dP/dt_{max}$ with CRT despite pronounced type 3 asynchrony (patients nos. 22 to 24).

TABLE 1

L-S Phase Relationship Types

| | Controls Subjects (n = 10) | Type 1 Patients (n = 4) | Type 2 Patients (n = 17) | Type 3 Patients (n = 13) |
|---|---|---|---|---|
| $\Phi_L$ | 148 ± 19° | 183 ± 35° | 202 ± 34°* | 183 ± 24°* |
| $\Phi_S$ | 167 ± 21° | 178 ± 32° | 125 ± 37°8† | 303 ± 35°*†‡ |
| $\Phi_{LS}$ | −19 ± 19° | 5 ± 6° | 77 ± 33°*† | −119 ± 31°*†‡ |
| QRS duration (ms) | 78 ± 9 | 134 ± 14* | 186 ± 33*† | 176 ± 30*† |
| Baseline $dP/dt_{max}$ (mmHg/s) | Not Done | 692 ± 310 | 532 ± 148 | 558 ± 154 |
| ?$dP/dt_{max}$ with optimized CRT | Not Done | 2 ± 1% | 26 ± 14%† | 18 ± 15% |

*p < 0.05 vs. control subjects.
†p < 0.05 vs. type 1 patinets.
‡p < 0.05 vs. type 2 patients. Data are presented as the mean value ± SD.)

TABLE 2

Non-Invasive Measures of Asynchrony and Individual Hemodynamic Response to CRT

| Patient* no. | Type | Baseline QRS Duration (ms) | Baseline $\Phi_{LS}$ (°) | Baseline $dP/dt_{max}$ (mmHg/s) | Best CRT ?$\Delta dp/dt_{max}$ (%) | Best CRT mode |
|---|---|---|---|---|---|---|
| 1 | 1 | 123† | 10.62 | 882.76 | 2.62 | NR |
| 2 | 1 | 124 | 7.08 | 411.92 | 0.42 | NR |
| 3 | 1 | 135 | −3.40 | 1028.15 | 2.19 | NR |
| 4 | 1 | 153 | 5.11 | 445.82 | 1.03 | NR |
| 5 | 2 | 128 | 64.68 | 674.02 | 16.86 | BV |
| 6 | 2 | 130 | 38.62 | 780.47 | 11.01 | BV |
| 7 | 2 | 160 | 37.97 | 597.49 | 28.67 | BV |
| 8 | 2 | 166 | 47.16 | 625.73 | 2.64 | NR |
| 9 | 2 | 169 | 44.49 | 434.46 | 27.91 | LV |
| 10 | 2 | 172 | 51.07 | 811.57 | 9.15 | LV |
| 11 | 2 | 176 | 105.14 | 470.20 | 39.62 | LV |
| 12 | 2 | 184 | 55.83 | 702.77 | 39.55 | BV |
| 13 | 2 | 191 | 115.55 | 396.71 | 16.16 | BV |
| 14 | 2 | 193 | 65.71 | 361.66 | 41.62 | BV |
| 15 | 2 | 193 | 109.17 | 487.61 | 32.01 | LV |
| 16 | 2 | 196 | 45.84 | 309.38 | 53.81 | LV |
| 17 | 2 | 198 | 91.66 | 519.63 | 10.29 | LV |
| 18 | 2 | 202 | 61.20 | 400.47 | 19.55 | LV |
| 19 | 2 | 210 | 127.04 | 522.32 | 25.00 | LV |
| 20 | 2 | 221 | 125.88 | 551.14 | 36.26 | LV |
| 21 | 2 | 268 | 118.53 | 405.94 | 34.92 | LV |
| 22 | 3 | 124 | −102.30 | 767.32 | 0.21 | NR |
| 23 | 3 | 128 | −120.52 | 847.35 | 0.55 | NR |
| 24 | 3 | 148 | −178.52 | 582.22 | 1.16 | NR |
| 25 | 3 | 168 | −104.95 | 590.91 | 20.35 | LV |
| 26 | 3 | 172 | −112.50 | 443.44 | 12.05 | LV |
| 27 | 3 | 178 | −61.84 | 775.26 | 19.45 | LV |
| 28 | 3 | 178 | −133.76 | 588.02 | 24.47 | BV |

TABLE 2-continued

Non-Invasive Measures of Asynchrony and
Individual Hemodynamic Response to CRT

| Patient* no. | Type | Baseline QRS Duration (ms) | Baseline $\Phi_{LS}$ (°) | Baseline dP/dt$_{max}$ (mmHg/s) | Best CRT ?Δdp/dt$_{max}$ (%) | Best CRT mode |
|---|---|---|---|---|---|---|
| 29 | 3 | 178 | −139.26 | 356.59 | 43.05 | LV |
| 30 | 3 | 181 | −76.86 | 486.32 | 6.64 | BV |
| 31 | 3 | 193 | −153.37 | 478.41 | 19.67 | LV |
| 32 | 3 | 194† | −99.76 | 424.16 | 46.87 | LV |
| 33 | 3 | 215 | −121.90 | 502.99 | 25.94 | LV |
| 34 | 3 | 228 | −138.46 | 407.97 | 16.09 | LV |

(*Patients are sorted by their QRS duration in each type group and assigned identifying numbers.
†Patients with right bundle branch block [RBBB]).

Figure 7:
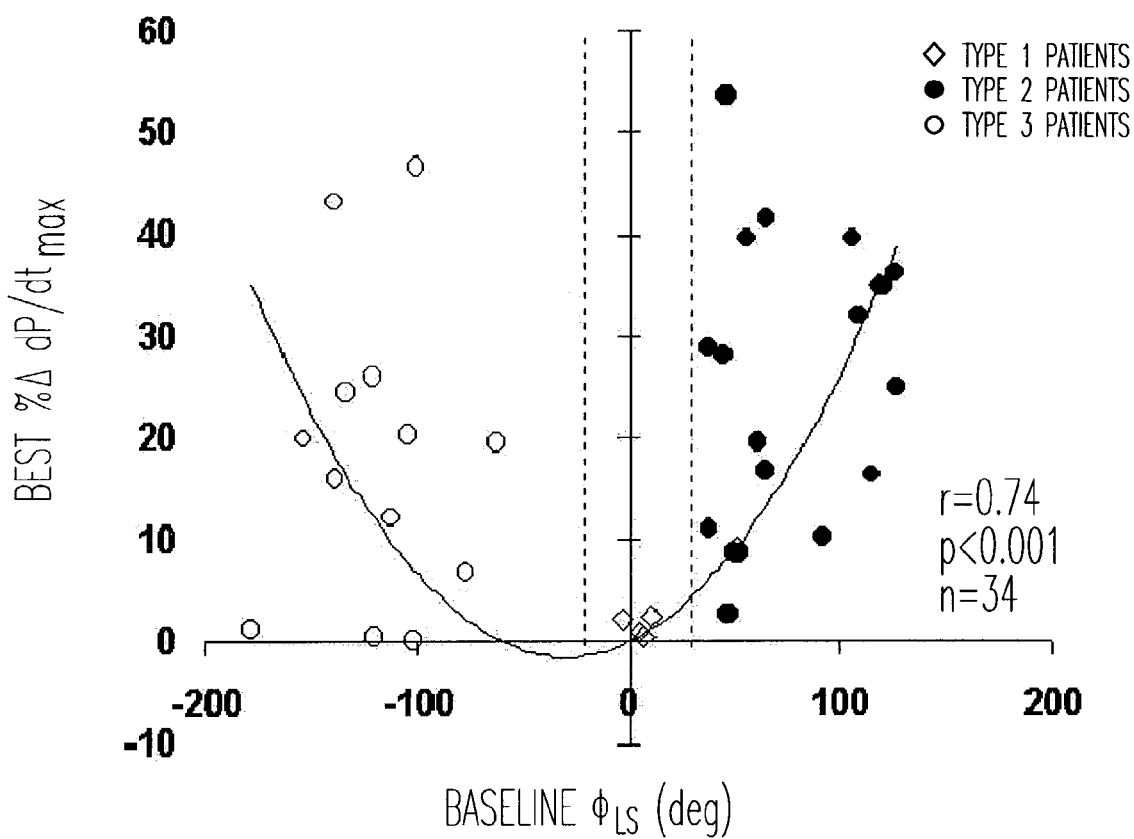
FIG. 7 is an illustration of an example of a unimodal relationship observed between each patient's hemodynamic response at the best cardiac resynchronization therapy setting for the patient and the patient's baseline difference between the patient's lateral and septal phase angles.

FIG. 7 include an example of a unimodal relationship that was observed between the dP/dt$_{max}$ response at the best possible CRT setting in each patient and their baseline $\Phi_{LS}$. In FIG. 7, data points are fitted by a regression analysis with a second-order polynomial forced to pass through the origin (0,0): % ΔdP/dt$_{max}$=0.098×(baseline $\Phi_{LS}$)+0.0016×(baseline $\Phi_{LS}$)$^2$. The correlation coefficient was calculated for a regression through the origin, and significance was tested with ANOVA ($R^2$=0.54, p<0.001). The vertical dashed lines separate the different types of wall motion patterns. As illustrated in FIG. 7, patients who exhibited large increases in dP/dt$_{max}$ at the best CRT setting tended to have large positive or negative baseline $\Phi_{LS}$ value, corresponding to a large degree of lateral-septal asynchrony. Patients who exhibited small increases in dP/dt$_{max}$ at the best CRT setting tended to have small baseline $\Phi_{LS}$ value, corresponding to more synchronous lateral-septal displacements.

No significant differences were observed between DCM and CAD patients, although those with DCM tended to show slightly larger QRS width at baseline (183±32 ms vs. 160±34 ms, p=0.07), a higher |$\Phi_{LS}$| (93±46° vs. 66±43°, p=0.13) and a larger hemodynamic response to CRT (22±15 mmHg/s vs. 16±15 mmHg/s, p=0.07).

Figure 8:
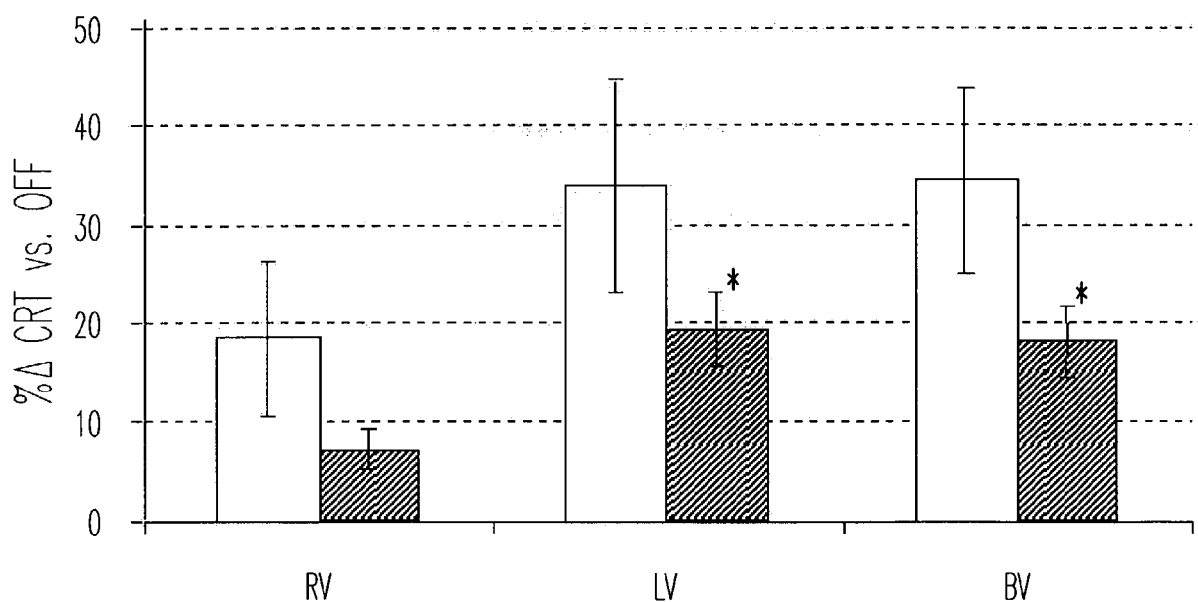
FIG. 8 is an illustration of patients' hemodynamic and wall motion responses to cardiac resynchronization therapy.
Figure 9A:
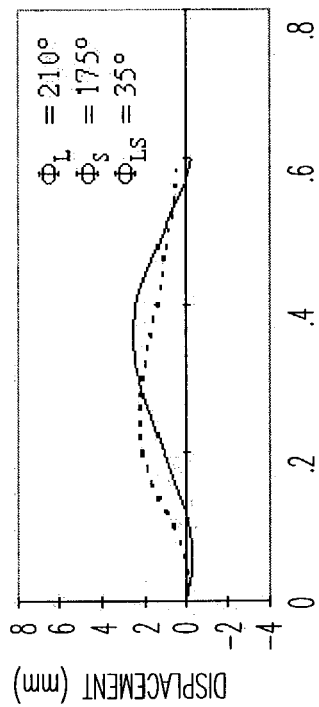
FIGS. 9A–D are illustrations of exemplary effects of cardiac resynchronization therapy on lateral and septal wall displacement curves.
Figure 9B:
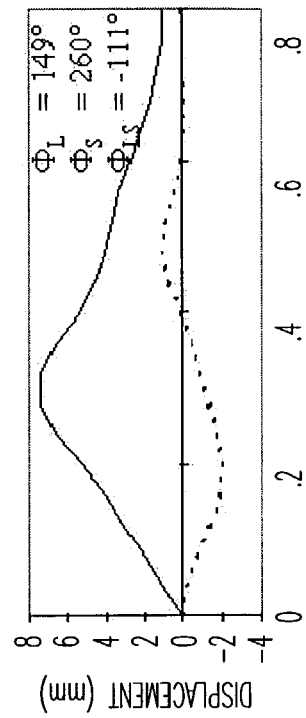
Figure 9C:
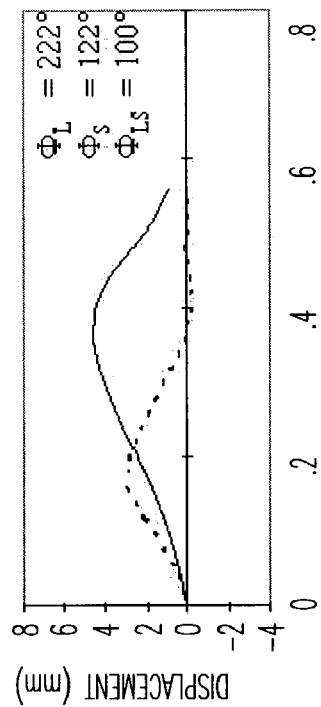
Figure 9D:
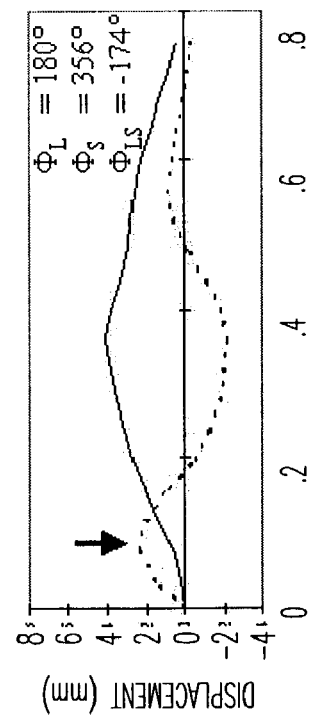

Effects of CRT on L-S synchrony. Sixteen patients were studied 4 weeks after implantation to test the early effects of CRT on mean L-S synchrony, as measured by the change in |$\Phi_{LS}$| during reprogramming of the pacemakers. During intrinsic conduction (OFF), mean |$\Phi_{LS}$| was 104±41°, which decreased to 86±45° with RV CRT (p=0.14 vs. OFF), to 71±50° with LV CRT (mean difference −33, 95% confidence interval [CI]−54 to −11, p=0.001 vs. OFF), and to 66±42° with BV CRT (mean difference −38, 95% CI−59 to −17, p=0.001 vs. OFF). FIG. 8 illustrates the improvement in |$\Phi_{LS}$| (open bars) and dP/dt$_{max}$ (shaded bars) displayed as the percent change from no pacing (OFF) for every CRT mode (RV, LV, and BV). The data are presented as the mean value±SEM (n=16, *p<0.001 vs. RV). As illustrated in FIG. 8, Percent synchrony improvement with each CRT mode was associated with proportional percentage increases in dP/dt$_{max}$. Compared with RV pacing, LV and BV pacing resulted in significantly larger increases in dP/dt$_{max}$ (p<0.001) and trended to have larger differences in synchrony improvement (p=0.14 vs. LV; p=0.12 vs. BV).

Figure 10A:
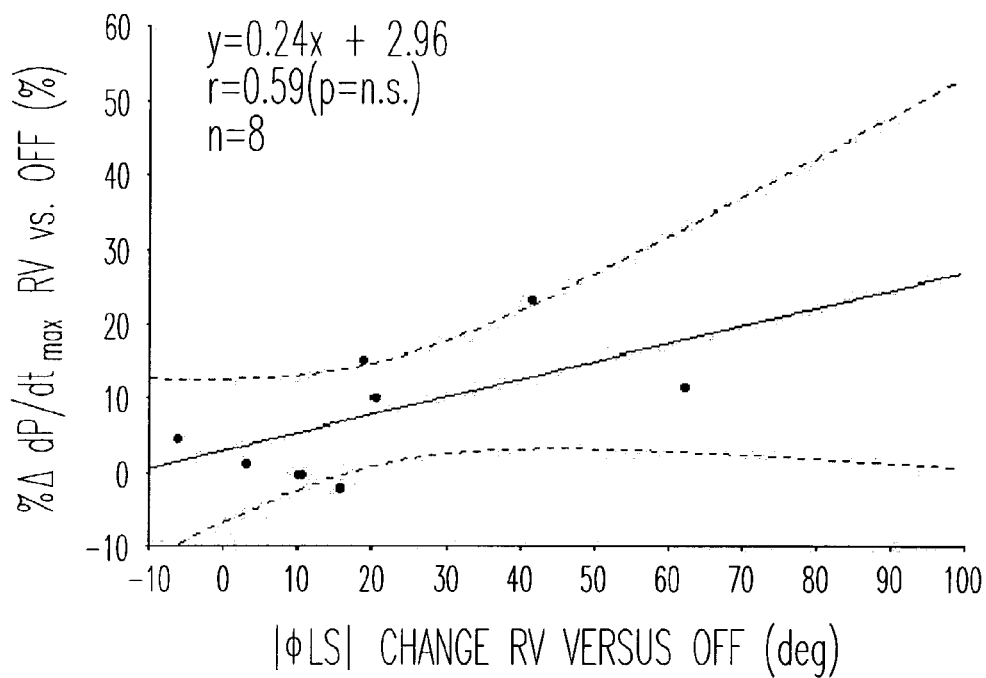
FIGS. 10A–C are illustrations of exemplary curves for predicting hemodynamic response based on the change in the difference between lateral and septal phase angles in response to cardiac resynchronization therapy.
Figure 10B:
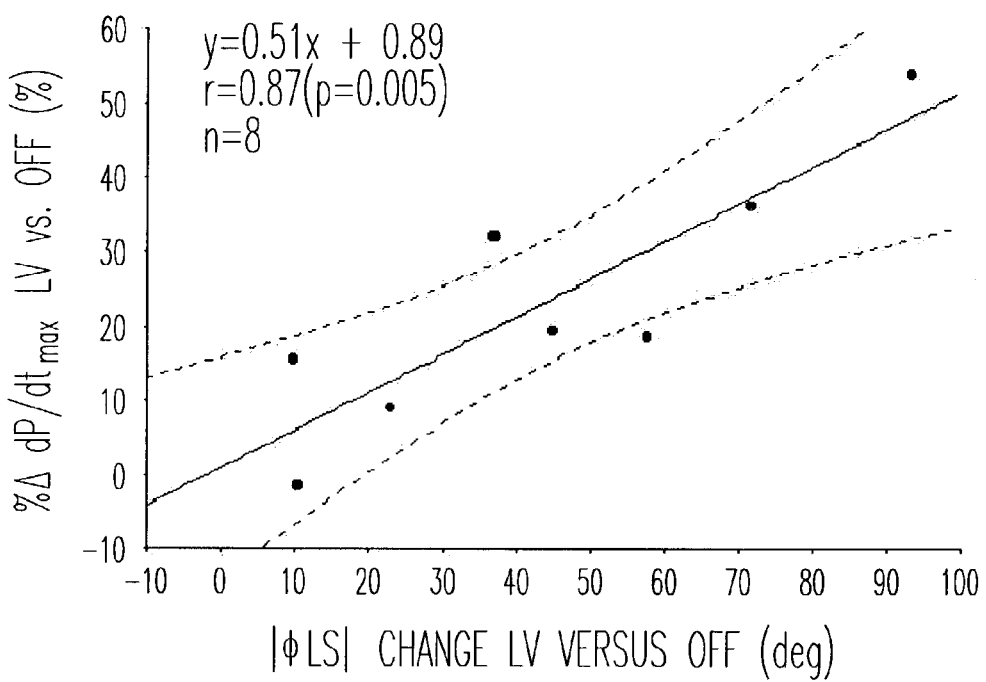
Figure 10C:
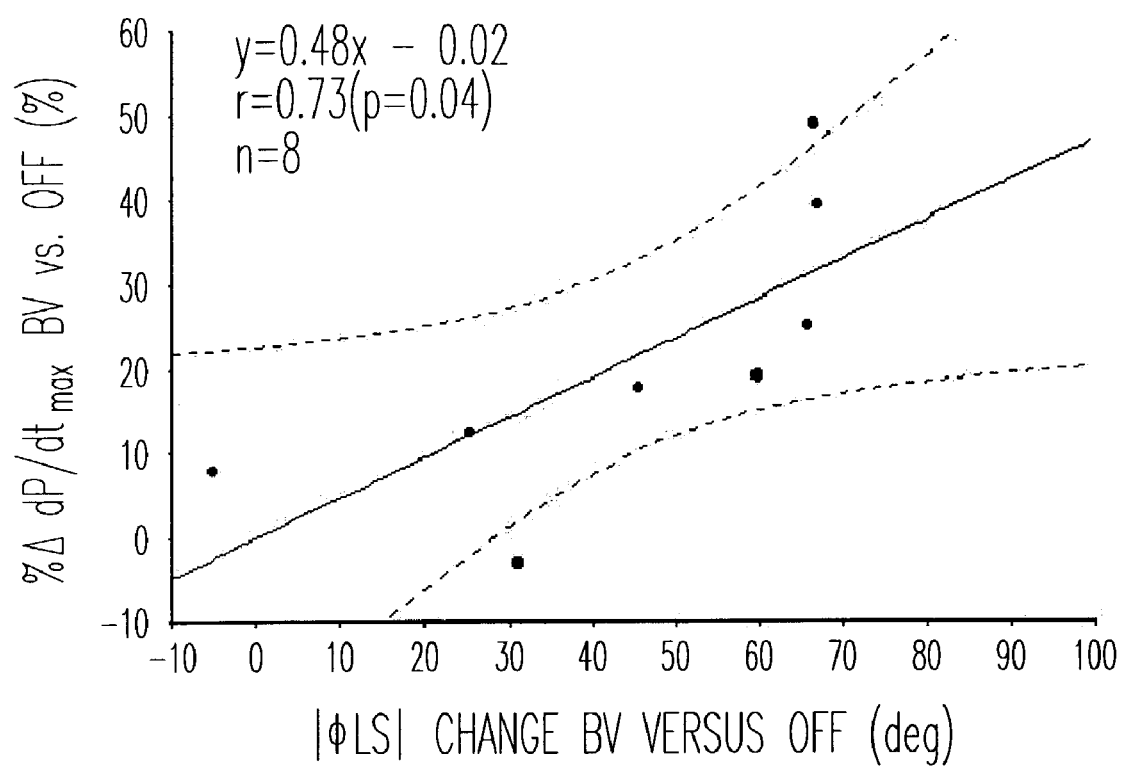

FIGS. 9A–D include examples of effect of CRT on lateral (solid line) and septal (dashed line) wall displacement curves. Type 2 patients (n=8) exhibited a significant |$\Phi_{LS}$| decrease from 84±26° (OFF) to 36±26° at the best CRT mode (p<0.001 vs. OFF by paired t-test) (e.g., FIGS. 9A and 9B). In contrast, type 3 patients (n=8) showed less change, with a non-significant |$\Phi_{LS}$| decrease from 123±46° (OFF) to 105±41° at the best CRT mode (p=NS by the paired t-test). However, CRT eliminated or reversed the early septal inward movement in type 3 patients (e.g., FIGS. 9C and 9D). FIGS. 10A–C include examples of the change in |$\Phi_{LS}$| with CRT predicting the improvement in dP/dt$_{max}$ in type 2 patients. The correlation between |$\Phi_{LS}$| and dP/dt$_{max}$ changes with CRT was significant for type 2 patients (n=8) who had LV and BV CRT (FIGS. 10B and 10C), but failed to reach significance for those who had RV CRT (FIG. 10A). No significant correlation between |$\Phi_{LS}$| and dP/dt$_{max}$ was observed in type 3 patients.

Reproducibility. A good reproducibility of phase angle analysis was found: 8±11° for repeated measurements (intraobserver variability) (adjusted to 180°: 5±6%) and 15±11° for two independent observers (interobserver variability) (adjusted to 180°: 8±6%).

Conclusions of the Study

The study demonstrates an echocardiographic phase analysis technique for quantifying LV mechanical wall motion synchrony to predict a hemodynamic contractile function benefit from CRT. Increased dP/dt$_{max}$ due to CRT was directly associated with improved LV mechanical synchrony, as measured by the reduction in the absolute L-S phase angle |$\Phi_{LS}$| in type 2 patients with delayed lateral wall inward movement. By two-dimensional echocardiography, this study also non-invasively assessed the effects of different CRT stimulation sites on LV mechanical synchrony and compared it to the invasively measured hemodynamic response. Both LV and BV CRT significantly improved LV L-S synchrony, whereas less improvement was observed with RV CRT. This is consistent with previous reports that LV and BV CRT increase dP/dt$_{max}$ to a much larger extent than RV CRT.

The absolute L-S phase angle |$\Phi_{LS}$| shows a direct relationship between invasively measured hemodynamic improvement with CRT and LV mechanical synchrony assessed by echocardiographic analysis of radial wall motion. Baseline asynchrony indicated by |$\Phi_{LS}$|>25° predicts contractile function benefit from CRT. For patients with type 2 L-S phase patterns, the magnitude of |$\Phi_{LS}$| reduction with CRT correlates to the invasively measured increase in dP/dt$_{max}$. The echocardiographic phase analysis technique may provide a non-invasive screening method for heart failure patients to select those likely to increase contractile function with CRT and to optimize CRT after implantation.

Phase Analysis Using Harmonic Frequency Phase Angles

In the phase analysis method discussed above, the fundamental frequency phase angle of the Fourier transform of a regional displacement curve is used to represent a cardiac regional displacement phase. The difference between two fundamental frequency phase angles provides for the quantitative measure of ventricular asynchrony. The method using the Fourier fundamental frequency phase angles is most suitable for patients characterized by monophasic regional wall displacement, i.e., a single inward-outward motion during a cardiac cycle. When a patient is characterized by biphasic or triphasic lateral and septal wall displacement, the method using the Fourier fundamental frequency phase angles may not provide for an adequate quantitative measure of ventricular asynchrony. For example, when the lateral phase angle $\Phi_L$ and septal phase angle $\Phi_S$ are fundamental frequency phase angles, $\Phi_{LS}$ does not indicate whether wall motion is characterized by monophasic, biphasic, or triphasic displacement. When $\Phi_{LS}$ is used to identify a therapy candidate, a value computed using the fundamental frequency phase angles may not predict, for example, whether CRT beneficially changes a wall motion pattern, such as by changing a triphasic displacement to a biphasic displacement.

Phase analysis using harmonic frequency phase angles, in addition to the fundamental frequency, of the Fourier transform of a regional displacement curve provides additional information quantifying ventricular asynchrony. In one embodiment, phase difference $\Phi'_{LS}$ calculated from $\Phi'_L$ and $\Phi'_S$, both first harmonic frequency phase angles, predicts substantial benefits of CRT to a patient when phase difference $\Phi_{LS}$ calculated based on the fundamental frequency phase angles fails to predict a substantial benefit. The method of echocardiographic quantification of ventricular asynchrony based on harmonic frequency phase angles is similar to the method including steps 200–280, as described with reference to FIG. 2 and FIG. 5, except that each regional phase angle, $\phi'$, is the phase angle of a harmonic frequency of the Fourier transform computed over the corresponding regional displacement curve. The phase difference quantifying the ventricular asynchrony is based on the harmonic frequency phase angles. In one embodiment, the harmonic frequency is the first harmonic frequency. In one embodiment, the method of echocardiographic quantification of ventricular asynchrony is based on computations of fundamental frequency phase angles and harmonic frequency phase angles. In one embodiment, the method of echocardiographic quantification of ventricular asynchrony is based on computations of only harmonic frequency phase angles.

Therapy Evaluation and Optimization

Figure 11A:
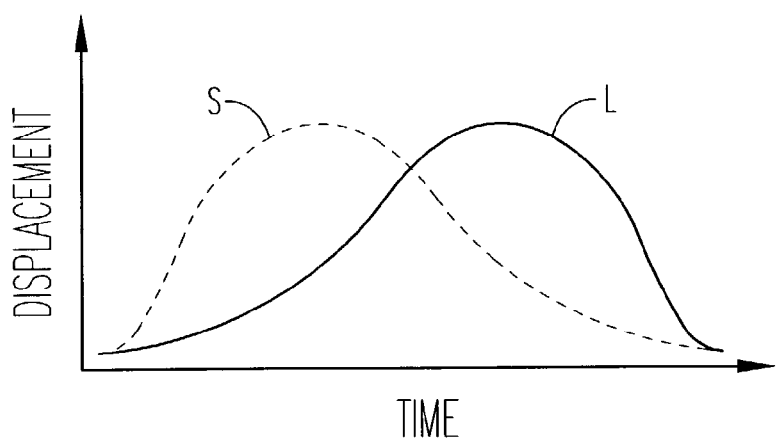
FIGS. 11A–C are illustrations of responses to therapies measurable by the echocardiographic quantification of ventricular asynchrony.
Figure 11B:
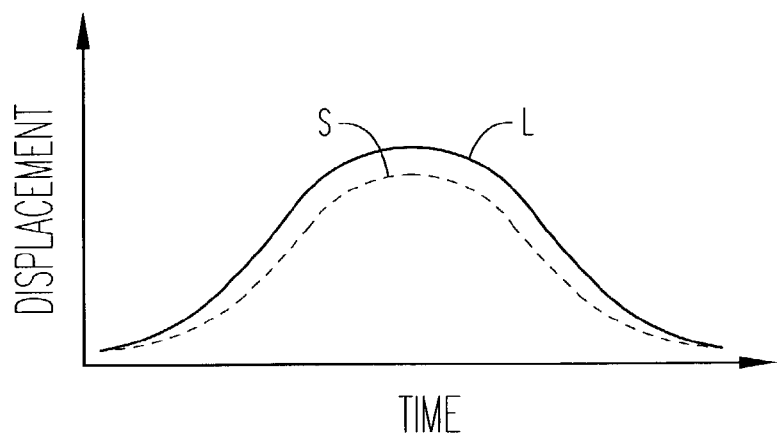
Figure 11C:
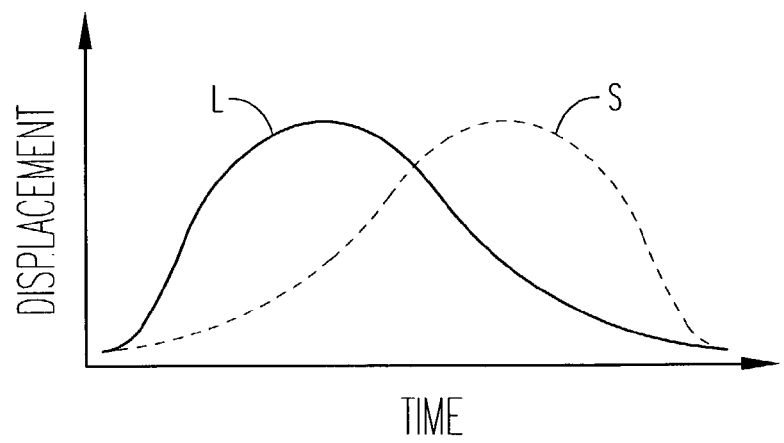

In one embodiment, the echocardiographic quantification of ventricular asynchrony is used to determine one or more therapy parameters that are approximately optimal for one or more intended responses to the therapy. FIGS. 11A–C are, by way of example, but not by way of limitation, illustrations of such intended responses to therapies measurable by the echocardiographic quantification of ventricular asynchrony. FIGS. 11A–C each include a septal wall displacement curve (S, dotted line) and a lateral wall displacement curve (L, solid line) for LV wall motion over one cardiac cycle. FIG. 11A is an illustration of one example of septal and lateral wall displacement curves of a patient having LBBB. In FIG. 11A, the septal wall displacement curve peaks substantially earlier than the lateral displacement curve, resulting in a substantially positive $\Phi_{LS}$, and hence, a decreased LV contractility and poor hemodynamic performance. A therapy is thus sought to increase the LV contractility by resynchronizing the LV wall motion. As illustrated in FIG. 11B, the intended response of the therapy is an approximately optimal contractility, or approximately maximum resynchronization, indicated by a minimum $|\Phi_{LS}|$. Furthermore, the heart of a patient having suffered LBBB for a significant period of time typically has a very thin septal wall because it is subject to early activation, low preload, and low stress, and very thick lateral wall because it is subject to later activation, high preload, and high stress. When the lateral wall contracts late, it is subject to a large stress. The large stress causes further deterioration of the muscles of the lateral wall. Another therapy is thus sought to force a shift in ventricular asynchrony by artificially activating the lateral wall to cause it to contract substantially earlier than the septal wall in each cardiac cycle. The shift in ventricular asynchrony transfers a substantial amount of the stress from the lateral wall to the septal wall. As illustrated in FIG. 11C, the intended response of the therapy is an approximately optimal stress reduction, or approximately maximum unloading of lateral wall stress, indicated by a minimum (most negative) $\Phi_{LS}$.

Figure 12:
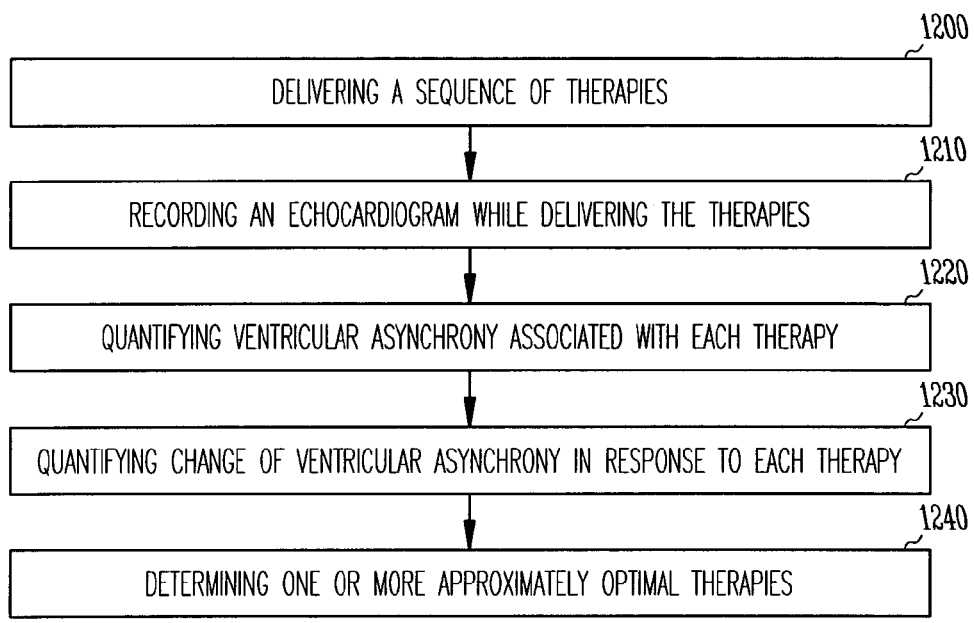
FIG. 12 is a flow chart illustrating one embodiment of a method for determining approximately optimal therapies based on the echocardiographic quantification of ventricular asynchrony.

FIG. 12 is a flow chart illustrating one embodiment of a method for determining approximately optimal therapies based on the echocardiographic quantification of ventricular asynchrony. A sequence of therapies is evaluated by quantifying ventricular asynchrony as response to each therapy. At 1200, a sequence of predetermined therapies is delivered to a patient. In one embodiment, programmer 140 includes a controller adapted to time the delivery of the sequence of therapies. Implanted device 110 includes a therapy circuit to deliver the sequence of therapies. The therapy circuit includes at least one of a pacing circuit, a defibrillation circuit, a CRT circuit, and a drug delivery circuit. In one embodiment, the sequence of predetermined therapies is defined using a therapy protocol describing each of the therapies and the timing of delivery. In one embodiment, the therapies are of the same therapy type but each include a therapy parameter that is distinctive from the other therapies in the sequence. In this embodiment, a sequence of therapy parameters is evaluated. The controller includes a therapy protocol synthesizer to generate the sequence of therapy parameters, and an automatic therapy protocol execution module to time the delivery according to the descriptions of the therapy protocol. In one embodiment, the therapy protocol defines an alternating therapy and non-therapy sequence. Delivery of each therapy follows a non-therapy period such that the response to each therapy can be isolated for analysis. At 1210, an echocardiogram is recorded while the sequence of predetermined therapies is delivered. In one embodiment, the echocardiogram is recorded while the automatic therapy protocol execution module executes a therapy protocol. At 1220, the patient's response to the delivery of each therapy is evaluated by quantifying the patient's ventricular asynchrony associated with the therapy based on analyzing the portion of the echocardiogram recorded during the delivery of the therapy. In one embodiment, the method discussed with reference to FIG. 2, including steps 200–280, is incorporated into step 1220. At 1230, the patient's response to each therapy delivered to the patient is quantified. In one embodiment, this includes quantifying a change of ventricular asynchrony. In one specific embodiment, quantifying the change of ventricular asynchrony includes quantifying a reduction in ventricular asynchrony in response to the delivery of each therapy. In another specific embodiment, quantifying the change of ventricular asynchrony includes quantifying a shift in ventricular asynchrony in response to the delivery of each therapy. The shift in ventricular asynchrony indicates that the order of regional displacement is changed during each cardiac cycle. In one specific embodiment, the shift in ventricular asynchrony is indicated by a change in the sign (between positive and negative) of $\Phi_{LS}$. In one embodiment, the method discussed with reference to FIG. 2, including steps 200–280, is incorporated into step 1230 for each non-therapy period preceding each therapy delivery. The change of ventricular asynchrony associated with each therapy is then quantified by computing a difference between the degree of the patient's ventricular asynchrony associated with the therapy and the degree of the patient's ventricular asynchrony associated with the non-therapy period preceding the delivery of the therapy. In one specific embodiment, this includes computing a difference, $\Delta\Phi_{LS}$, between the value of $\Phi_{LS}$ associated with the therapy and the value of $\Phi_{LS}$ associated with the non-therapy period before the delivery of the therapy. At 1240, one or more approximately optimal therapies are determined. In one embodiment, one or more approximately optimal therapies are selected from the sequence of predetermined therapies. In one embodiment, an approximately optimal therapy is a therapy, among the sequence of predetermined therapies, that results in a minimum degree of ventricular asynchrony. In one specific embodiment, the approximately optimal therapy is the therapy that results in a minimum $\Phi_{LS}$. In another embodiment, an approximately optimal therapy is a therapy, among the sequence of predetermined therapies, that results in a maximum difference between the degree of the patient's ventricular asynchrony associated with the therapy and the degree of the patient's ventricular asynchrony associated with non-therapy (i.e., the baseline). In one specific embodiment, the approximately optimal therapy is the therapy that results in a maximum change in $\Delta\Phi_{LS}$. In one embodiment, an approximately optimal therapy is determined to provide for the approximately optimal ventricular contractility, or approximately maximum ventricular resynchronization, indicative by the maximum reduction of ventricular asynchrony resulted from the sequence of therapies. In one embodiment, one approximately optimal therapy is determined to provide for the approximately optimal stress reduction, or approximately maximum unloading of wall stress, indicated by a maximum shift of ventricular asynchrony resulted from the sequence of therapies.

Figure 13:
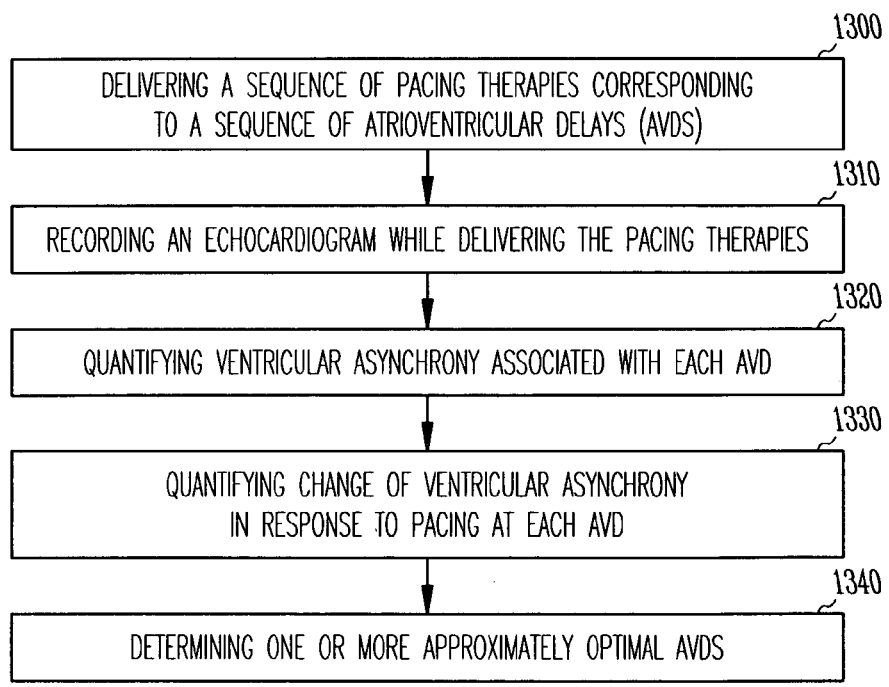
FIG. 13 is a flow chart illustrating one embodiment of a method for determining approximately optimal atrioventricular delay (AVD) based on the echocardiographic quantification of ventricular asynchrony.

FIG. 13 is a flow chart illustrating one embodiment of a method for determining approximately optimal AVDs based on the echocardiographic quantification of ventricular asynchrony. In one embodiment, degree of ventricular asynchrony is controllable by pacing with one or more selected AVDs. For example, a patient with LBBB has a degenerated LV conduction system in which the propagation of the action potentials is blocked in some or all of fast conducting Purkinje fibers, which in a normal heart allow the action potentials to activate the lateral wall. Consequently, the septal wall contracts substantially earlier than the lateral wall. The resultant ventricular asynchrony reduces the efficiency of the heart's pumping functions, or hemodynamic performance, and preloads a large portion of the lateral wall, which is then subject to high stress when it contracts. LV pacing with one or more predetermined AVDs changes the relative timing of the septal and lateral wall contraction to at least partially correct the problems associated with the ventricular asynchrony and/or excessive loading on the lateral wall.

A sequence of predetermined AVDs is evaluated by quantifying ventricular asynchrony as response to a sequence of pacing therapies each using one of the predetermined AVDs. At 1300, the sequence of pacing therapies is delivered to a patient. In one embodiment, programmer 140 includes a controller adapted to time the delivery of the sequence of pacing therapies. Implanted device 110 includes a therapy circuit. The therapy circuit includes at least a pacing circuit to deliver the sequence of pacing therapies. In one embodiment, the sequence of pacing therapies is defined using a pacing protocol describing each of the pacing therapies, and the timing of delivery. The controller includes a therapy protocol synthesizer to generate the sequence of predetermined AVDs, and an automatic therapy protocol execution module to time the delivery of pacing therapy according to the descriptions of the pacing protocol. In one embodiment, the therapy protocol synthesizer includes an AVD calculator to calculate the sequence of predetermined AVDs based on a cardiac time interval measured from the patient. In one embodiment, the pacing protocol includes description of an alternating pacing and non-pacing sequence. Delivery of each pacing therapy follows a non-pacing period such that the response to each therapy can be isolated for analysis. At 1310, an echocardiogram is recorded while the sequence of pacing therapies is delivered. In one embodiment, the echocardiogram is recorded while the automatic therapy protocol execution module executes the pacing protocol. At 1320, the patient's response to the delivery of each pacing therapy is evaluated by quantifying the patient's ventricular asynchrony associated with the AVD used in the pacing therapy based on analyzing the portion of the echocardiogram recorded during the delivery of the pacing therapy. In one embodiment, the method discussed with reference to FIG. 2, including steps 200–280, is incorporated into step 1320. At 1330, the patient's response to each pacing therapy is evaluated. In one embodiment, this includes quantifying a change of ventricular asynchrony associated with each AVD. In one specific embodiment, quantifying the change includes quantifying a reduction of ventricular asynchrony associated with each AVD. In another specific embodiment, quantifying the change includes quantifying a shift in ventricular asynchrony associated with each AVD. The shift in ventricular asynchrony indicates that the order of regional displacement is changed during each cardiac cycle, indicated by a change in the sign (between positive and negative) of $\Phi_{LS}$. In one embodiment, the method discussed with reference to FIG. 2, including steps 200–280, is incorporated into step 1330 for each non-therapy period preceding each therapy delivery. The change of ventricular asynchrony associated with AVD is then quantified by computing a difference between the degree of the patient's ventricular asynchrony associated with the AVD and the degree of the patient's ventricular asynchrony associated with the non-therapy period preceding the delivery of the pacing therapy at the AVD. In one specific embodiment, this includes computing a difference, $\Phi_{LS}$ between the value of $\Phi_{LS}$ associated with the AVD and the value of $\Phi_{LS}$ associated with the non-therapy period before the delivery of the pacing therapy at the AVD. At 1340, one or more approximately optimal AVDs are determined. In one embodiment, an AVD selector selects one or more approximately optimal AVDs from the sequence of predetermined AVDs. In another embodiment, one or more approximately optimal AVDs are calculated from, or otherwise based on, the sequence of the predetermined AVDs. In one embodiment, an approximately optimal AVD is determined to provide for the approximately optimal LV contractility, or approximately maximum LV resynchronization, indicated by the maximum reduction of ventricular asynchrony resulted from the sequence of pacing therapies. In one embodiment, an approximately optimal AVD is an AVD, among the sequence of predetermined AVDs, that results in a minimum degree of ventricular asynchrony. In one specific embodiment, the approximately optimal AVD is the AVD that results in a minimum $|\Phi_{LS}|$. In another embodiment, an approximately AVD is an AVD, among the sequence of predetermined AVDs, that results in a maximum difference between the degree of the patient's ventricular asynebrony associated with the therapy and the degree of the patient's ventricular asynchrony associated with non-therapy (i.e., the baseline). In one specific embodiment, the approximately optimal AVD is the AVD that results in a maximum change in $\Delta\Phi_{LS}$. In one embodiment, an approximately optimal AVD is determined to provide for the approximately optimal stress reduction, or approximately maximum unloading of wall stress, indicated by a maximum shift of ventricular asynclirony resulted from the sequence of pacing therapies.

In one embodiment, an approximately optimal AVD is an AVD, among the sequence of predetermined AVDs, that results in a minimum (most negative) $\Phi_{LS}$.

Figure 14:
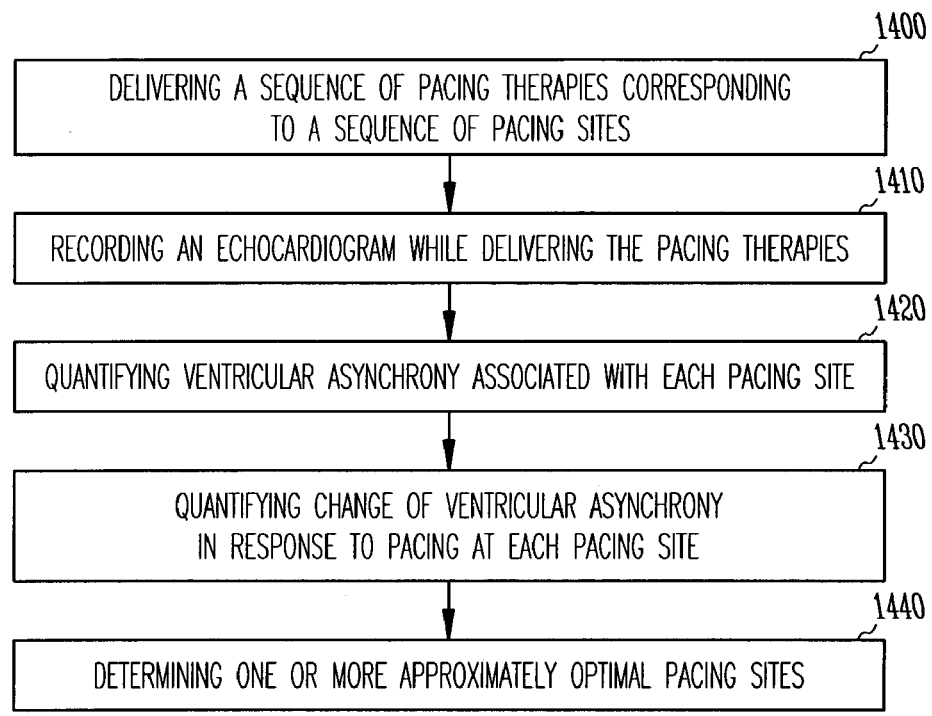
FIG. 14 is a flow chart illustrating one embodiment of a method for determining approximately optimal pacing site or pacing site combination based on the echocardiographic quantification of ventricular asynchrony.

FIG. 14 is a flow chart illustrating one embodiment of a method for determining approximately optimal pacing sites based on the echocardiographic quantification of ventricular asynchrony. In one embodiment, degree of ventricular asynchrony is controllable by pacing at one or more selected pacing sites. Pacing at the one or more selected pacing sites replaces or supplements an abnormal conduction system with conduction blocks or excessive delays at certain cardiac regions.

A sequence of predetermined pacing sites and/or pacing site combinations is evaluated by quantifying ventricular asynchrony as response to a sequence of pacing therapies each delivered to one of the predetermined pacing site or pacing site combination. The pacing sites and pacing site combinations may include any one or more of the pacing sites in heart 102 that are accessible via lead system 105. When a pacing therapy is delivered to more than one pacing site, the predetermined pacing site combination specifies the pacing sites as well as a relative timing for pacing pulse delivery with respect to each and every pacing site. In one embodiment, the pacing therapy includes delivering pacing pulses to all the pacing sites of the pacing site combination approximately simultaneously. In another embodiment, the pacing therapy includes delivering pacing pulses to the pacing sites with one or more inter-site pacing delays. For example, if a pacing therapy is to be delivered to two pacing sites, RV and LV, a "predetermined pacing site combination" specifies the pacing sites (RV and LV), the order by which the two sites are paced (LV first, RV first, or simultaneously), and the delay between the deliveries of pacing pulses to the two sites. Thus, in this document, each "pacing site combination" refers to not only a set of pacing sites but also the relative timing of pacing pulse delivery with respect to each pacing site. For example, "RV and LV with 40 ms interventricular delay (LV first)" and "RV and LV with −40 ms interventricular delay (RV first)" are two different pacing site combinations.

At 1400, the sequence of pacing therapies is delivered to a patient. In one embodiment, programmer 140 includes a controller adapted to time the delivery of the sequence of pacing therapies. Implanted device 110 includes a therapy circuit. The therapy circuit includes at least a pacing circuit to deliver the sequence of pacing therapies. In one embodiment, the sequence of pacing therapies is defined using a pacing protocol describing each of the pacing therapies, and the timing of delivery. The controller includes a therapy protocol synthesizer to generate the sequence of pacing sites and/or pacing site combinations, and an automatic therapy protocol execution module to time the delivery of pacing therapy according to the descriptions of the pacing protocol. In one embodiment, the pacing protocol includes description of an alternating pacing and non-pacing sequence. Delivery of each pacing therapy follows a non-pacing period such that the response to each therapy can be isolated for analysis. At 1410, an echocardiogram is recorded while the sequence of pacing therapies is delivered. In one embodiment, the echocardiogram is recorded while the automatic therapy protocol execution module executes the pacing protocol. At 1420, the patient's response to the delivery of each pacing therapy is evaluated by quantifying the patient's ventricular asynchrony associated with the pacing site or pacing site combination based on analyzing the portion of the echocardiogram recorded during the delivery of the pacing therapy.

In one embodiment, the method discussed with reference to FIG. 2, including steps 200–280, is incorporated into step 1420. At 1430, the patient's response to each pacing therapy is evaluated. In one embodiment, this includes quantifying a change of ventricular asynchrony associated with each pacing site or pacing site combination. In one specific embodiment, quantifying the change includes quantifying a reduction of ventricular asynchrony associated with each pacing site or pacing site combination. In another specific embodiment, quantifying the change includes quantifying a shift in ventricular asynchrony associated with each pacing site or pacing site combination. The shift in ventricular asynchrony indicates that the order of regional displacement is changed during each cardiac cycle, indicated by a change in the sign (between positive and negative) of $\Phi_{LS}$. In one embodiment, the method discussed with reference to FIG. 2, including steps 200–280, is incorporated into step 1430 for each non-therapy period preceding each therapy delivery. The change of ventricular asynchrony associated with each pacing site or pacing site combination is then quantified by computing a difference between the degree of the patient's ventricular asynchrony associated with the pacing site or pacing site combination and the degree of the patient's ventricular asynchrony associated with the non-therapy period preceding the delivery of the pacing therapy at the pacing site or pacing site combination. In one specific embodiment, this includes computing a difference, $\Phi_{LS}$ between the value of $\Phi_{LS}$ associated with the pacing site or pacing site combination and the value of $\Phi_{LS}$ associated with the non-therapy period before the delivery of the pacing therapy at the pacing site or pacing site combination. At 1440, one or more approximately optimal pacing sites or pacing site combinations are determined. In one embodiment, a pacing site selector selects one or more approximately optimal pacing sites or pacing site combinations from the sequence of pacing sites and/or pacing site combinations. In one embodiment, an approximately optimal pacing site or pacing site combination is determined to provide for the approximately optimal LV contractility, or approximately maximum LV resynchronization, indicated by the maximum reduction of ventricular asynchrony resulted from the sequence of pacing therapies. In one embodiment, an approximately optimal pacing site or pacing site combination is a pacing site or pacing site combination, among the sequence of pacing sites and/or pacing site combinations, that results in a minimum degree of ventricular asynchrony. In one specific embodiment, the approximately optimal pacing site or pacing site combination is the pacing site or pacing site combination that results in a minimum $|\Phi_{LS}|$. In another embodiment, an approximately optimal pacing site or pacing site combination is a pacing site or pacing site combination, among the sequence of predetermined pacing sites or pacing site combinations, that results in a maximum difference between the degree of the patient's ventricular asynchrony associated with the therapy and the degree of the patient's ventricular asynchrony associated with non-therapy (i.e., the baseline). In one specific embodiment, the approximately optimal pacing site or pacing site combination is the pacing site or pacing site combination that results in a maximum change in $\Delta\Phi_{LS}$. In one embodiment, an approximately optimal pacing site or pacing site combination is determined to provide for the approximately optimal stress reduction, or approximately maximum unloading of wall stress, indicated by a maximum shift of ventricular asynchrony resulted from the sequence of pacing therapies. In one embodiment, an approximately optimal pacing site or pacing site combination is pacing site or pacing site combination, among the sequence of predetermined pacing sites or pacing site combinations, that results in a minimum (most negative) $\Phi_{LS}$.

A pacing protocol defining a sequence of pacing therapies with different pacing parameter combinations allows evaluation of multiple pacing parameters by one pacing protocol execution. In one embodiment, a pacing protocol defines a sequence of predetermined AVDs, a sequence of predetermined pacing sites and/or pacing site combinations, and a sequence of predetermined combinations of the two parameters selected from the two sequences. In one specific example, pacing therapies using each AVD is delivered to each of pacing sites and/or pacing site combinations. The method described above with reference to FIGS. 13 and 14 then allows the selection of an approximately optimal combination of an AVD and a pacing site or pacing site combination following one pacing protocol execution.

The evaluation of AVD and pacing sites are examples of pacing therapy parameters that can be evaluated using the echocardiographic quantification of ventricular asynchrony. Embodiments for evaluating other pacing parameters, as well as pacing parameter combinations, will be apparent to those of skill in the art upon reviewing the above description.

Therapy Determination Based on Baseline Echocardiographic Analysis

Figure 15:
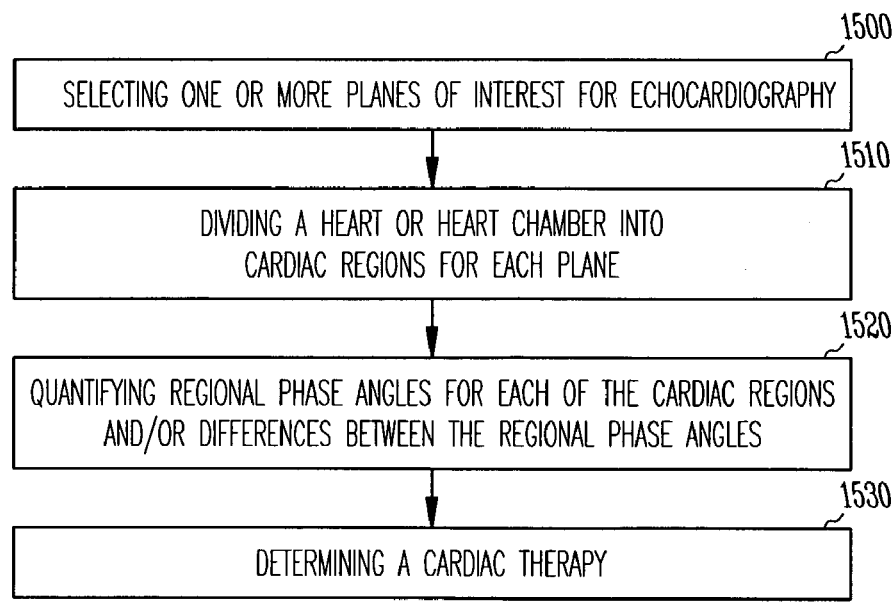
FIG. 15 is a flow chart illustrating one embodiment of a method for determining a therapy based on prediction of therapeutic benefits using the echocardiographic quantification of ventricular asynchrony.

The echocardiographic analysis for quantification of cardiac wall motion asynchrony also provides for a method for predicting the benefits of a therapy to a patient based on that patient's baseline data. That is, the benefit of a therapy is predictable without actually delivering the therapy for the purpose of prediction. One specific application is, by way of example, but not by way of limitation, to predict whether a patient will likely benefit from a CRT. In one embodiment, one or more therapy parameters are determined by predicting therapeutic benefits using the echocardiographic quantification of ventricular asynchrony without the need to evaluate the therapy by actually delivering the therapy. FIG. 15 is a flow chart illustrating one embodiment of such a method. At 1500, one or more cross-sectional image planes are selected, according to which echocardiographic sensor 160 is oriented for recording an echocardiogram for each plane. At 1510, a heart, or a portion of the heart such as a particular heart chamber, is divided into cardiac regions. In one embodiment, the division depends on how a potential therapy or therapy parameter will be controlled if the patient is predicted to benefit from the therapy. In one specific embodiment, the division depends on possible sites where a pacing electrode potentially will be disposed. At 1520, the method discussed with reference to FIG. 2, including steps 200–270 or 200–280, is incorporated to quantify regional phase angles for each of the cardiac regions or differences between regional phase angles, respectively. An echocardiogram is recorded for each of the one or more cross-sectional planes. For each plane, regional endocardial wall displacements are calculated. For each region, a regional phase angle is computed. In one embodiment, a relative regional phase angle for each region is computed as the difference between the regional phase angle for the region and the regional phase angle for another predetermined region. At 1530, a therapy is recommended or determined by predicting the benefits of the therapy by observing all the computed regional phase angles or relative rational phase angles. In one specific embodiment, whether a patient will likely benefit from CRT is predicted based on the averaged septal and lateral wall displacement curves, such as those illustrated in FIGS. 6A–D. The type 2 (FIG. 6C) and type 3 (FIG. 6D) patterns support a prediction that the patient will likely benefit from CRT, and the type 1 pattern does not support the same prediction because the septal and lateral displacements are already substantially synchronized. In one specific embodiment, whether a patient will benefit from CRT is predicted based on whether the patients baseline $|\Phi_{LS}|$ exceeds a predetermined $|\Phi_{LS}|$ threshold. Referring to FIG. 7, for example, patients who exhibit large increases in dP/dt$_{max}$ at the best CRT setting tend to have large baseline $|\Phi_{LS}|$ value, corresponding to a large degree of lateral-septal asynchrony and therefore predicting a likelihood of benefit from CRT. Patients who exhibit small increases in dP/dt$_{max}$ at the best CRT setting tend to have small baseline $|\Phi_{LS}|$ value, corresponding to more synchronous lateral-septal displacements and therefore predicting an unlikelihood of benefit from CRT. In one specific embodiment, the predetermined $|\Phi_{LS}|$ threshold is 25 degrees. In one embodiment, the benefits of a therapy is predicted based on the knowledge accumulated by performing the therapy evaluation and optimization methods described above with respect to FIGS. 12–14. The determination of the therapy includes, by way of example, but not by way of limitation, determination of pacing site or pacing site combination (which includes timing for therapy delivery with respect to each pacing site, such as inter-site pacing delays), AVD, other pacing parameters, and combinations thereof. In one embodiment, the therapy is determined to change an overall degree of ventricular asynchrony for a ventricular chamber. In another embodiment, the therapy is determined to change a degree of ventricular asynchrony as observed in one selected cross-sectional plane. In yet another embodiment, the therapy is determined to change the phase angle of a selected cardiac region relative to another selected cardiac region.

CONCLUSION

This document describes an echocardiographic analysis method and apparatus for quantification of cardiac wall motion asynchrony. It is to be understood that the above detailed description is intended to be illustrative, and not restrictive. For example, the present method and apparatus of echocardiographic analysis may be generally employed in evaluation and/or management of heart conditions that involve quantification of cardiac wall motion. The present method can also be performed using an external pacing system that performs functions similar to those of system 100, with a percutaneous lead system providing electrical connection to the heart. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system, comprising:
   a curve generator adapted to generate first and second regional displacement curves based on magnitudes of cardiac regional wall displacement over a cardiac cycle length interval for first and second cardiac regions, respectively;
   a curve offset module, coupled to the curve generator, to provide a common magnitude reference for the first and second regional wall displacement curves;

a curve averager, coupled to the curve offset module, to average each of the first and second regional displacement curves over a predetermined number of cardiac cycles;

a curve smoothing module, coupled to the curve averager, to smooth the averaged first and second regional displacement curves; and a phase computer coupled to the curve smoothing module, the phase computer adapted to compute a relative phase representing a phase relationship between the first and second regional displacement curves based on a frequency analysis, the relative phase indicative of a cardiac wall motion asynchrony.

2. The system of claim 1, wherein the curve smoothing module comprises a moving average filter.

3. The system of claim 1, wherein the phase computer comprises:

a regional displacement phase calculator coupled to the curve smoothing module, the regional displacement phase calculator adapted to calculate first and second regional displacement phase angles based on Fourier transforms of the first and second regional displacement curves, respectively; and a relative phase calculator, coupled to the regional displacement phase calculator, to calculate the relative phase being a difference between the first and second phase angles.

4. The system of claim 3, wherein the regional displacement phase calculator comprises a fundamental frequency phase calculator to calculate a phase angle at a fundamental frequency for each of the Fourier transforms of the first and second regional displacement curves.

5. The system of claim 3, wherein the regional displacement phase calculator comprises a harmonic phase calculator to calculate a phase angle at a harmonic frequency for each of the Fourier transforms of the first and second regional displacement curves.

6. The system of claim 3, wherein the regional displacement phase calculator includes a septal wall displacement phase calculator to calculate a septal phase angle $\Phi_S$ and a lateral wall displacement phase calculator to calculate a lateral phase angle $\Phi_L$.

7. The system of claim 6, wherein the relative phase calculator includes a difference calculator to calculate the phase difference: $\Phi_{LS}=\Phi_L-\Phi_S$.

8. The system of claim 7, further comprising a therapy decision module coupled to the relative phase calculator, the therapy decision module adapted to predict a benefit of a predetermined therapy based on $\Phi_{LS}$.

9. The system of claim 8, wherein:

the relative phase calculator calculates an absolute value of $\Phi_{LS}$: $|\Phi_{LS}|$; and the therapy decision module comprises a therapy decision comparator to compare $|\Phi_{LS}|$ to a predetermined threshold.

10. The system of claim 7, further comprising:

a controller including:

a therapy protocol synthesizer adapted to generate a sequence of therapy parameters; and an automatic therapy protocol execution module adapted to time delivery of a sequence of therapies each using at least one parameter of the sequence of therapy parameters; and a therapy circuit, coupled to the controller, to deliver the sequence of therapies, wherein the curve generator is adapted to generate the first and second regional displacement curves using a portion of an echocardiogram recorded during the delivery of each therapy of the sequence of therapies, and the relative phase calculator is adapted to calculate values of $\Phi_{LS}$ each associated with the each therapy of the sequence of therapies.

11. The system of claim 10, wherein the therapy circuit comprises a cardiac pacing circuit, and the therapy protocol synthesizer comprises an atrioventricular delay (AVD) calculator to calculate a sequence of AVDs each being used in one therapy of the sequence of therapies.

12. The system of claim 11, further comprising an AVD selector to select an AVD associated with an approximately maximum ventricular resynchronization from the sequence of AVDs based on the values of $\Phi_{LS}$ calculated for the sequence of therapies.

13. The system of claim 12, wherein the relative phase calculator is adapted to calculate absolute values of $\Phi_{LS}$ each associated with one therapy of the sequence of therapies, and the AVD selector is adapted to select an AVD associated with a minimum value of the absolute values of $\Phi_{LS}$ calculated for the sequence of therapies.

14. The system of claim 11, further comprising an AVD selector to select an AVD associated with an approximately optimal unloading of stress on the lateral wall from the sequence of AVDs based on the values of $\Phi_{LS}$ calculated for the sequence of therapies.

15. The system of claim 14, wherein the AVD selector is adapted to select an AVD associated with a negative $\Phi_{LS}$.

16. The system of claim 10, wherein the therapy circuit comprises a cardiac pacing circuit, and the therapy protocol synthesizer is adapted to generate a sequence of pacing sites each being used in one therapy of the sequence of therapies, the pacing sites each defined by parameters specifying one or more sites and timing of pacing pulse delivery with respect to each of the one or more sites.

17. The system of claim 16, further comprising an pacing site selector to select a pacing site or pacing site combination associated with an approximately maximum ventricular resynchronization from the sequence of pacing sites based on the values of $\Phi_{LS}$ calculated for the sequence of therapies.

18. The system of claim 17, wherein the relative phase calculator is adapted to calculate absolute values of $\Phi_{LS}$ each associated with one therapy of the sequence of therapies, and the pacing site selector is adapted to select a pacing site or pacing site combination associated with a minimum value of the absolute values of $\Phi_{LS}$ calculated for the sequence of therapies.

19. The system of claim 16, further comprising a pacing site selector to select a pacing site or pacing site combination associated with an approximately optimal unloading of stress on a ventricular wall from the sequence of pacing sites based on the values of $\Phi_{LS}$ calculated for the sequence of therapies.

20. The system of claim 19, wherein the pacing site selector is adapted to select a pacing site or pacing site combination associated with a negative $\Phi_{LS}$.

* * * * *

UNITED STATES PATENT AND TRADEMARK OFFICE
CERTIFICATE OF CORRECTION

PATENT NO.         : 7,041,061 B2
APPLICATION NO. : 10/402324
DATED                 : May 9, 2006
INVENTOR(S)       : Kramer et al.

It is certified that error appears in the above-identified patent and that said Letters Patent is hereby corrected as shown below:

In column 13, line 40, delete "ins," and insert - - ms, - -, therefor.

In column 14, line 4, delete "groun" and insert - - group - -, therefor.

In column 14, line 42, delete "?$\Delta dp/dt_{max}$" and insert - - $\Delta dP/dt_{max}$ - -, therefor.

In column 15, line 8, delete "?$\Delta dp/dt_{max}$" and insert - - $\Delta dP/dt_{max}$ - -, therefor.

In column 18, line 6, delete "detennining" and insert - - determining - -, therefor.

In column 18, line 59, delete "asvchrony" and insert - - asynchrony - -, therefor.

In column 20, line 30, after "with" insert - - each - -.

In column 20, line 37, before "between" delete "$\Phi_{LS}$" and insert - - $\Delta\Phi_{LS,}$ - - therefor.

In column 20, line 58, delete "asynebrony" and insert - - asynchrony - - , therefor.

In column 20, line 67, delete "asynclirony" and insert- - asynchrony - -, therefor.

In column 21, line 43, delete "natient, In" and insert - - patient.  In - -, therefor.

In column 21, line 65, delete "asynebrony" and insert - - asynchrony - -, therefor.

In column 22, line 23, delete "natient's" and insert - - patient's - -, therefor. `

UNITED STATES PATENT AND TRADEMARK OFFICE
CERTIFICATE OF CORRECTION

PATENT NO. : 7,041,061 B2
APPLICATION NO. : 10/402324
DATED : May 9, 2006
INVENTOR(S) : Kramer et al.

It is certified that error appears in the above-identified patent and that said Letters Patent is hereby corrected as shown below:

In column 22, line 27, delete "$\Phi_{LS}$" and insert -- $\Delta\Phi_{LS,}$ -- therefor.

Signed and Sealed this

Twenty-eighth Day of November, 2006

JON W. DUDAS
*Director of the United States Patent and Trademark Office*